US012403262B2

(12) United States Patent
Murray et al.

(10) Patent No.: US 12,403,262 B2
(45) Date of Patent: *Sep. 2, 2025

(54) TAMPER EVIDENT ASSEMBLY WITH RFID FOR SYRINGES

(71) Applicant: Fresenius Kabi USA, LLC, Lake Zurich, IL (US)

(72) Inventors: Christopher J. Murray, Chicago, IL (US); Anthony Ferraro, Vernon Hills, IL (US); Gang Ju, Vernon Hills, IL (US); Robert Speek, Highland Park, IL (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 1104 days.

This patent is subject to a terminal disclaimer.

(21) Appl. No.: 17/235,919

(22) Filed: Apr. 20, 2021

(65) Prior Publication Data

US 2021/0236736 A1 Aug. 5, 2021

Related U.S. Application Data

(63) Continuation-in-part of application No. 16/408,947, filed on May 10, 2019, now Pat. No. 11,305,072.
(Continued)

(51) Int. Cl.
*A61M 5/31* (2006.01)
*A61M 5/32* (2006.01)
(Continued)

(52) U.S. Cl.
CPC ........ *A61M 5/3134* (2013.01); *A61M 5/3202* (2013.01); *A61M 5/5086* (2013.01); *G06K 19/0723* (2013.01); *A61M 2005/3118* (2013.01)

(58) Field of Classification Search
CPC ........ A61M 5/5086; A61M 2005/3118; A61M 5/3134; A61M 5/3202; A61M 2005/3104;
(Continued)

(56) References Cited

U.S. PATENT DOCUMENTS 4,174,238 A 11/1979 Fowles et al.
4,667,837 A 5/1987 Vitello et al.
(Continued)

FOREIGN PATENT DOCUMENTS

EP 0716860 A2 6/1996
EP 0766975 A1 4/1997
(Continued)

OTHER PUBLICATIONS

International Patent Application No. PCT/US2019/063283; Int'l Search Report and the Written Opinion; dated Apr. 2, 2020; 28 pages.
(Continued)

*Primary Examiner* — Jason E Flick
(74) *Attorney, Agent, or Firm* — Blank Rome LLP

(57) ABSTRACT

The present disclosure describes a syringe assembly including a syringe including a Luer connection and a tip, a plunger, a tip cap, a tamper evident cap disposed over the tip cap, a film including a frangible connection, and an RFID tag. The film secures the tamper evident cap to the Luer connection, where the frangible connection can break under a force applied to the tamper evident cap such that the tamper evident cap disengages from the Luer connection when the frangible connection breaks. The RFID tag is disposed on the syringe and has an integrated circuit and an antenna configured to send/receive signals between an RFID reader.

25 Claims, 13 Drawing Sheets

Related U.S. Application Data

(60) Provisional application No. 62/772,461, filed on Nov. 28, 2018.

(51) Int. Cl.
*A61M 5/50* (2006.01)
*G06K 19/07* (2006.01)
*G06K 19/077* (2006.01)

(58) Field of Classification Search
CPC .............. A61M 2005/312; A61M 5/50; A61M 2005/3103; A61M 2005/3106; A61M 2005/3114; A61M 2005/3117; A61M 2207/00; G06K 19/0723; G06K 19/07798; G06K 19/07758
USPC ....................................................... 604/111
See application file for complete search history.

(56) References Cited

U.S. PATENT DOCUMENTS

| | | |
|---|---|---|
| 5,135,496 A | 8/1992 | Vetter et al. |
| 5,322,515 A | 6/1994 | Karas et al. |
| 5,328,474 A | 7/1994 | Raines |
| 5,554,134 A | 9/1996 | Bonnichsen |
| 5,624,402 A * | 4/1997 | Imbert ................ A61M 5/3134 604/533 |
| 5,649,622 A | 7/1997 | Hollister |
| 5,680,945 A | 10/1997 | Sander et al. |
| 5,785,691 A | 7/1998 | Vetter et al. |
| 5,833,653 A | 11/1998 | Vetter et al. |
| 5,851,200 A | 12/1998 | Higashikawa et al. |
| 5,944,699 A | 8/1999 | Barrelle et al. |
| 5,989,227 A | 11/1999 | Vetter et al. |
| 6,193,688 B1 | 2/2001 | Balestracci et al. |
| 6,196,998 B1 | 3/2001 | Jansen et al. |
| 6,330,959 B1 | 12/2001 | Dark |
| 6,432,088 B1 | 8/2002 | Huang et al. |
| 6,485,460 B2 | 11/2002 | Eakins et al. |
| 6,491,665 B1 | 12/2002 | Vetter et al. |
| 6,520,935 B1 | 2/2003 | Jansen et al. |
| 6,585,691 B1 | 7/2003 | Vitello |
| 6,726,652 B2 | 4/2004 | Eakins et al. |
| 6,846,303 B2 | 1/2005 | Eakins et al. |
| 6,942,643 B2 | 9/2005 | Eakins et al. |
| 7,144,238 B2 | 12/2006 | Chao |
| 7,374,555 B2 | 5/2008 | Heinz et al. |
| 7,488,307 B2 | 2/2009 | Rimlinger et al. |
| 7,632,244 B2 | 12/2009 | Buehler et al. |
| 7,806,861 B2 | 10/2010 | Witowski |
| 8,075,535 B2 | 12/2011 | Carrel et al. |
| 8,348,895 B1 * | 1/2013 | Vitello ................ A61M 5/5086 215/253 |
| 8,353,869 B2 | 1/2013 | Ranalletta et al. |
| 8,591,462 B1 | 11/2013 | Vitello |
| 8,784,377 B2 | 7/2014 | Ranalletta et al. |
| 9,174,010 B2 | 11/2015 | Vedrine |
| 9,480,801 B2 | 11/2016 | Schiller et al. |
| 9,579,463 B2 | 2/2017 | Okihara |
| 9,731,082 B2 | 8/2017 | Vernizeau et al. |
| 9,758,281 B2 | 9/2017 | Glaser et al. |
| 9,821,152 B1 | 11/2017 | Vitello et al. |
| 9,925,340 B2 | 3/2018 | Glocker |
| 9,937,301 B2 | 4/2018 | Ward |
| 10,039,887 B2 | 8/2018 | Sundquist et al. |
| 10,124,122 B2 | 11/2018 | Zenker |
| 10,661,030 B1 | 5/2020 | Murray et al. |
| 11,305,072 B2 | 4/2022 | Murray et al. |
| 11,964,142 B2 | 4/2024 | Murray et al. |
| 2001/0003150 A1 | 6/2001 | Imbert |
| 2003/0014018 A1 | 1/2003 | Giambattista et al. |
| 2004/0116858 A1 | 6/2004 | Heinz et al. |
| 2004/0133169 A1 | 7/2004 | Heinz et al. |
| 2004/0225258 A1 | 11/2004 | Balestracci |
| 2008/0300550 A1 | 12/2008 | Schiller et al. |
| 2009/0283493 A1 | 11/2009 | Witowski |
| 2011/0015578 A1 * | 1/2011 | Lowke ................ A61M 5/5086 604/403 |
| 2012/0029438 A1 | 2/2012 | Vernizeau et al. |
| 2012/0037266 A1 * | 2/2012 | Bochenko ............. A61J 1/2096 604/404 |
| 2012/0111368 A1 | 5/2012 | Rahimy et al. |
| 2013/0237911 A1 * | 9/2013 | Von Schuckmann ........................ A61M 39/045 604/111 |
| 2013/0338604 A1 | 12/2013 | Roedle |
| 2014/0155827 A1 * | 6/2014 | Ostrander ............. G16H 10/65 604/93.01 |
| 2014/0262883 A1 | 9/2014 | Devouassoux et al. |
| 2015/0343155 A1 | 12/2015 | Zenker et al. |
| 2016/0001015 A1 | 1/2016 | Kucuk et al. |
| 2016/0151584 A1 | 6/2016 | Deleuil et al. |
| 2016/0184529 A1 * | 6/2016 | Okihara ................ A61M 5/28 604/199 |
| 2016/0200484 A1 | 7/2016 | Cosman |
| 2017/0049954 A1 * | 2/2017 | Edwards ................ A61M 5/19 |
| 2018/0273261 A1 | 9/2018 | Qiu |
| 2019/0099557 A1 | 4/2019 | Potdar et al. |
| 2019/0161229 A1 | 5/2019 | Mase |
| 2021/0236744 A1 | 8/2021 | Murray et al. |

FOREIGN PATENT DOCUMENTS

| | | | |
|---|---|---|---|
| EP | 1410819 A1 | | 4/2004 |
| EP | 2826508 A1 | | 1/2015 |
| EP | 2900301 A1 | | 8/2015 |
| EP | 3381492 A1 | | 10/2018 |
| JP | 2002315827 A | * | 10/2002 |
| WO | 2014049097 A1 | | 4/2014 |
| WO | 2018024624 A1 | | 2/2018 |
| WO | 2020112797 A1 | | 6/2020 |
| WO | 2020112807 A1 | | 6/2020 |

OTHER PUBLICATIONS

Schreiner press release, Cap-Lock Security Label with RFID Technology | Schreiner Group), "Digital Medication Management plus First-Opening Indication: Cap-Lock Security Label with RFID Technology", https://www.schreiner-group.com/en/company/press/press-releases/cap-lock-security-label-with-rfid-technology/, Oct. 27, 2020.

* cited by examiner

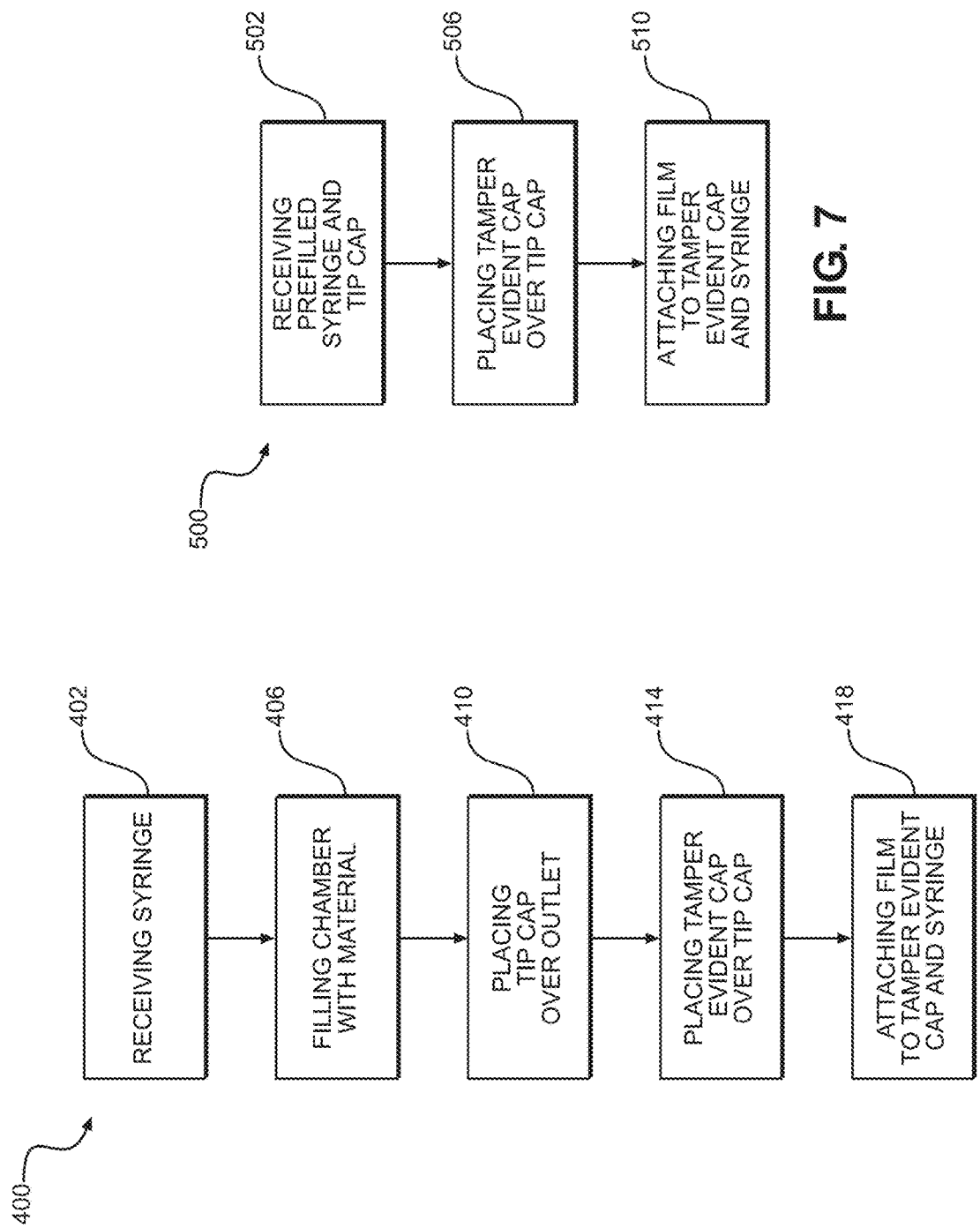

TAMPER EVIDENT ASSEMBLY WITH RFID FOR SYRINGES

CROSS REFERENCE TO RELATED APPLICATIONS

This application is a continuation-in-part of U.S. patent application Ser. No. 16/408,947, filed May 10, 2019, which is claims the benefit of U.S. Provisional Patent App. No. 62/772,461, filed Nov. 28, 2018, the disclosures of which are hereby incorporated by reference herein.

TECHNICAL FIELD

The present disclosure generally relates to tamper detection devices, and, more particularly, to a tamper evident cap and film with RFID capabilities for detecting tampering of syringes filled with a material.

BACKGROUND

Syringe assemblies are used to hold, transport, and deliver materials. For example, syringes are often utilized in medical environments to administer one or more medicinal materials. Syringe assemblies may differ in size, and their specific dimensions are dictated by the desired application and the specific material to be administered. In some instances, syringes may be pre-filled with one or more materials that are then dispensed from the syringe and combined with other elements.

Many industrial applications require mechanisms that prevent tampering with a particular product. This is especially the case with syringes used in the medical profession, where it is important for medical staff and patients to be aware of any tampering with the syringe or the material contained therein. Existing technology for detecting and preventing tampering is often cumbersome, difficult to use, increases risks of injury to the user, and increases the likelihood of contaminating the patient or the medical environment. Further, the addition of a tampering device can often require changes to be made to the manufacturing process of a syringe or its constituent components, which increases associated production costs and complexity of manufacturing.

Therefore, there is a need for tamper evident assembly configured to be used with syringes having preexisting designs that are filled with a material.

Some industrial applications require identification or tracking of devices and materials. Within the medical field, it is important for staff to be aware of usage parameters of various medical devices or materials for proper storage, handling, and administration to patients. Existing technology for tracking medical devices and materials often relies on manual control and monitoring, which increase the likelihood of human error during the process. The existing technology is not automated, and tracking parameters cannot be easily controlled over the lifetime of the device or material. Furthermore, implementing such control processes after the device or material has been manufactured and prepared requires additional steps to be performed by the medical staff, as well as implementation of separate equipment and operating protocols.

Accordingly, there is a need for an identification and monitoring system configured to be used with medical devices, such as syringes filled with a medical material.

SUMMARY

An embodiment of the present disclosure is syringe assembly comprising a syringe having a barrel body that extends from a proximal end to a distal end and defines a chamber extending along an axial direction therethrough, a Luer connection at the distal end, and a tip extending from the distal end along the axial direction and defining an outlet in fluid communication with the chamber, where the chamber contains a material. The syringe assembly also includes a plunger received within the chamber of the syringe to create a fluid seal within the barrel body, a tip cap defining a central passage configured to receive a portion of the tip such that the tip cap creates a fluid seal over the outlet, and a tamper evident assembly. The tamper evident assembly includes a tamper evident cap disposed over the tip cap, where the tamper evident cap has a main body that defines a proximal end defining an opening, a distal end opposite the proximal end along the axial direction, an outer surface, and an inner surface opposite the outer surface that defines a passage configured to receive the tip cap. The tamper evident assembly further includes a film including a frangible connection and configured to secure the tamper evident cap to the Luer connection, where the frangible connection is configured to break under a force applied to the tamper evident cap such that the tamper evident cap is configured to disengage from the Luer connection when the frangible connection breaks. The tamper evident assembly further includes a radio-frequency identification (RFID) tag disposed on the syringe and configured to receive and store data related to the syringe assembly. The RFID tag includes an integrated circuit, configured to store electronic information thereon, and an antenna operatively connected to the integrated circuit and configured to receive a signal from an RFID reader to cause transmission of the electronic data to or from the integrated circuit.

Another embodiment of the present disclosure is a method of labeling a syringe assembly. The method comprises providing a label configured to be affixed to a syringe. The label includes a radio-frequency identification (RFID) tag, and the RFID tag has an integrated circuit and an antenna operatively connected to the integrated circuit. The method also includes transmitting a first set of data to the RFID tag and storing the first set of data in a memory of the integrated circuit of the RFID tag. The method also includes verifying the first set of data on the RFID tag. The method further includes transmitting a second set of data to the RFID tag and storing the second set of data in the integrated circuit, the second set of data being different from the first set of data.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In the drawings:

FIG. 6 illustrates a process flow diagram of a method of filling a syringe with a material according to another embodiment of the present disclosure;

FIG. 7 illustrates a process flow diagram of a method of applying a tamper evident cap and film to a prefilled syringe according to an embodiment of the present disclosure;

DETAILED DESCRIPTION OF ILLUSTRATIVE EMBODIMENTS

Figure 1:
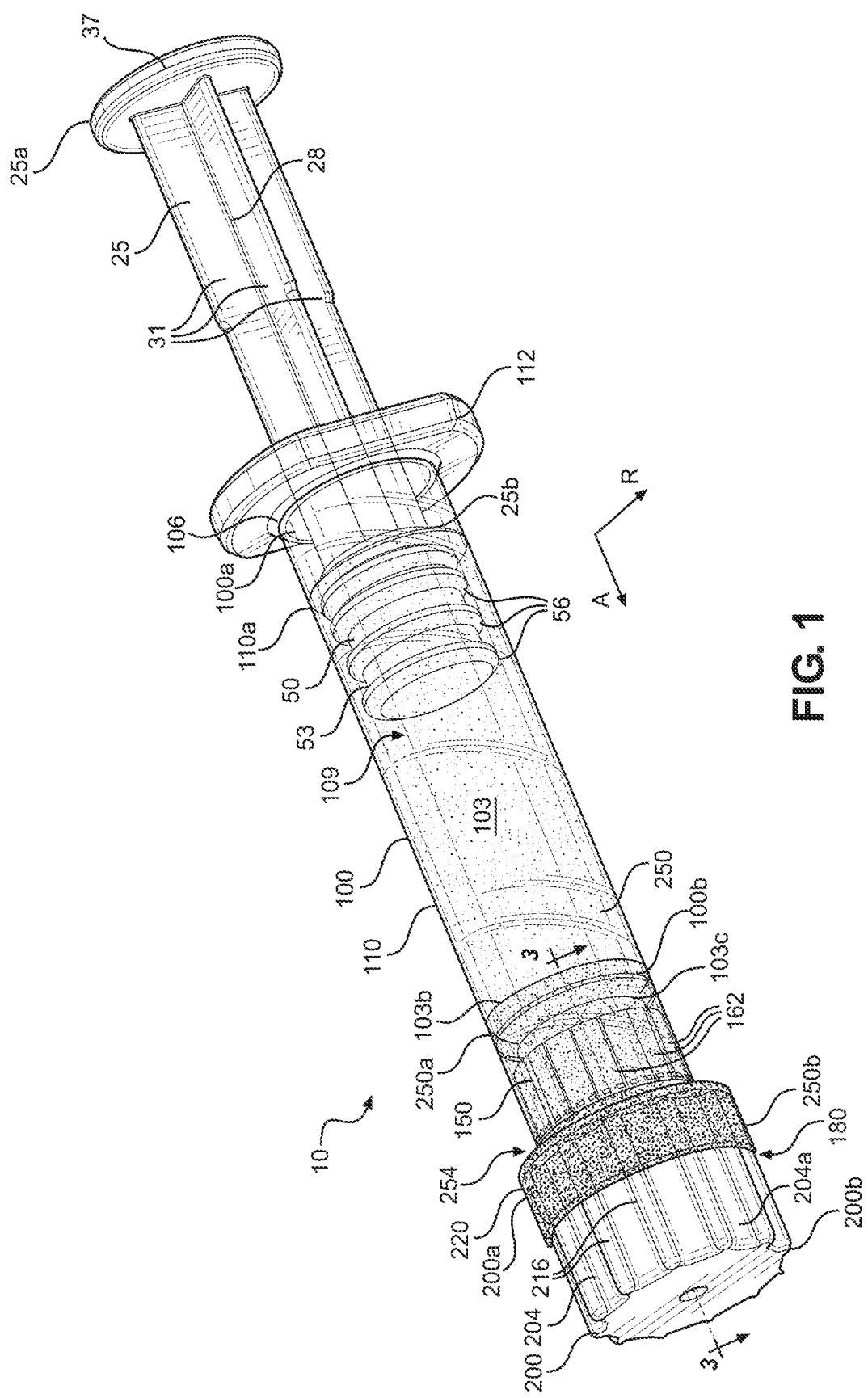
FIG. 1 illustrates a perspective view of a syringe assembly in accordance with an embodiment of the present disclosure.

Described herein is a syringe assembly 10 that includes a tamper evident assembly 180 including a tamper evident cap 200 and a film 250. Certain terminology is used to describe the syringe assembly 10 in the following description for convenience only and is not limiting. The words "right," "left," "lower," "upper," "lower," "proximal," and "distal" designate directions in the drawings to which reference is made. The words "inner" and "outer" refer to directions toward and away from, respectively, the geometric center of the description to describe the syringe assembly 10 and related parts thereof. The words "axially" and "radially" refer to directions along the orthogonal axial and radial directions A, R, respectively. The terminology includes the above-listed words, derivatives thereof and words of similar import.

Referring to FIGS. 1-4, the syringe assembly 10 includes a syringe 100 having a barrel body 103. The barrel body 103 can extend from a proximal end 100a to a distal end 100b along the axial direction A. The barrel body 103 can be molded from glass in one embodiment, though other materials are contemplated. For example, the barrel body 103 can be molded from cyclic olefin copolymer (COC), cyclic olefin polymer (COP), or various other plastic materials. In one embodiment, the barrel body 103 can comprise a substantially transparent material, such that a user of the syringe assembly 10 can monitor the material levels within the barrel body 103, though barrel bodies 103 having various levels of opacity are contemplated. The barrel body 103 is depicted as comprising a substantially cylindrical shape, though the present disclosure is not intended to be limited as such. The barrel body 103 can have an outer surface 103a that extends from the proximal end 100a to the distal end 100b along the axial direction A, an inner surface 103b opposite the outer surface 103a that also extends from the proximal end 100a to the distal end 100b along the axial direction A, and a distal surface 103c that extends substantially along the radial direction R at the distal end 100b of the barrel body 103. The inner surface 103b of the barrel body 103 defines a chamber 109 that extends along the axial direction A from an opening 106 at the proximal end 100a to the tip 126 at the distal end 100b. The chamber 109 is configured to receive and store a material, such as a liquid, for dispensing through the tip 126. The syringe assembly 10 further includes a Luer connection 140 at the distal end 100b of the barrel body 103, where the Luer connection 140 will be discussed further below. The syringe 100 also includes a flange 112 extending radially outwards from the proximal end 100a of the barrel body 103, where the function of the flange 112 will be described further below. Though depicted as defining an oval shape with two flat, oppositely positioned sides, the flange 112 can define other shapes as desired.

The chamber 109 can be sized and configured to receive a plunger 50, such that the plunger 50 is capable of sliding along the axial direction A through the chamber 109. The plunger 50 can have a substantially cylindrical body 53, though the shape of the body 53 will generally conform to the shape of the chamber 109. The body 53 can be comprised of a substantially flexible material such as rubber, though other embodiments are contemplated where the plunger 50 comprises other materials. The plunger 50 can further include a plurality of ridges 56 extending radially outwards from the body 53. As shown, the plurality of ridges 56 extend substantially circumferentially around the body 53 and are aligned and spaced apart along the axial direction A. However, the ridges 56 can comprise different sizes, shapes, and arrangements in other embodiments. The ridges 56 can function to engage the inner surface 103b of the barrel body 103 of the syringe so as to create a fluid seal between the plunger 50 and the syringe 100. As the plunger 50 moves distally through the chamber 109, the plunger 50 can function to push material out of the chamber 109 through the tip 126. Alternatively, as the plunger 50 moves proximally through the chamber 109, the plunger 50 can function to draw material into the chamber 109 through the tip 126.

The plunger 50 can define a bore that extends into the body 53 from its proximal end. The bore can be configured to engage a plunger rod 25 by any suitable means, e.g., screw fit, simple interference fit, snap-fit, or barbed engagement. The plunger rod 25 extends from a proximal end 25a to a distal end 25b opposite the proximal end 25a along the axial direction A. The plunger rod 25 can comprise a rod body 28 at its center, where the rod body 28 comprises an elongated, axially-extending rod. Connected to the rod body 28, the plunger rod 25 can include a plurality of walls 31 extending radially outwards from the rod body 28. As depicted, each of the walls 31 comprises multiple sections that each extend from the rod body 28 by various distances. However, other embodiments of the wall 31 are contemplated. For example, each of the walls 31 can define a substantially rectangular body that extends radially outwards from the rod body 28 and axially along the length of the rod body 28. The plunger rod 25 is shown as including four walls 31, where the walls 31 are arranged about the rod body 28 circumferentially spaced apart 90 degrees, such that the arrangement of walls 31 forms a substantially plus-shaped orientation. However, the plunger rod 25 can include more or less walls 31 in other embodiments, and thus other arrangements of walls 31 can define other shapes. Additionally, it is contemplated that the walls 31 can define other shapes or extend to different extents along the axial length of the rod body 28 or radially outwards from the rod body 28. The walls 31 can function to provide stability and strength to the plunger rod 25, while minimizing the cross-sectional footprint of the plunger rod 25 so as to reduce material requirements for the plunger rod 25, thus reducing overall weight of the syringe assembly 10.

Once the plunger 50 and the distal end 25b of the plunger rod 25 are inserted into the chamber 109 of the syringe 100, and the proximal end 25a of the plunger rod 25 is located outside the chamber 109, the plunger rod 25 can be used to control dispensing of the material from within the chamber 109. In operation, movement of the plunger rod 25, and thus the plunger 50, distally through the chamber 109 along the axial direction A forces material to flow out of the chamber 109 through the tip 126. To do this, a user can, using one hand, pull the flange 112 of the syringe 100 and a flange 37 of the plunger rod 25 towards each other. Conversely, movement of the plunger rod 25, and thus the plunger 50, proximally through the chamber 109 along the axial direction A draws material into the chamber 109 through the tip 126. To do this, a user can, using one or two hands, push the flange 112 of the syringe 100 and the flange 37 of the plunger rod 25 away from each other.

Figure 2:
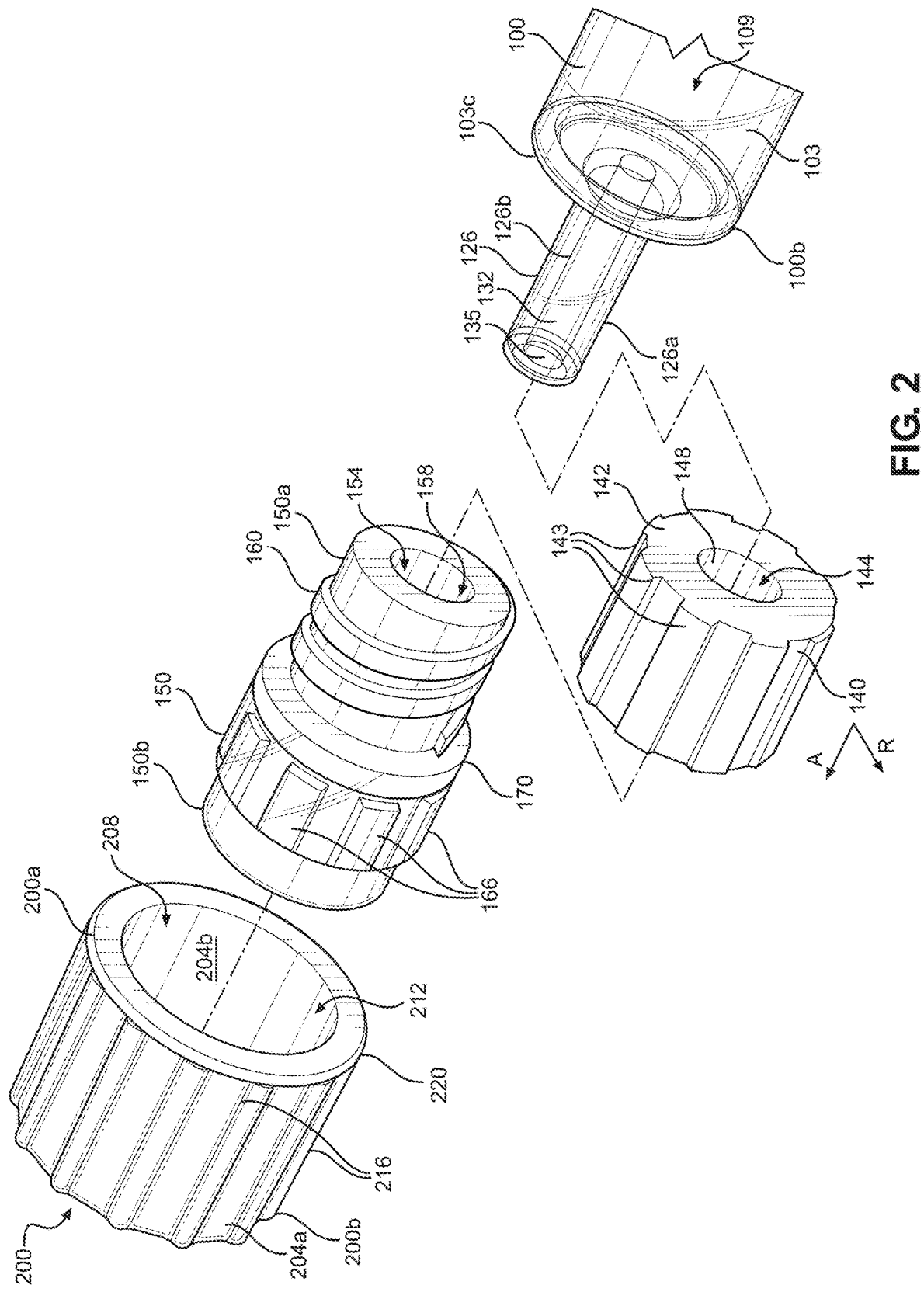
FIG. 2 illustrates an exploded view of a distal portion of the syringe assembly shown in FIG. 1.

Now referring to FIGS. 2-3, a Luer connection 140 of the syringe assembly 10 will be described in greater detail. In some embodiments, the Luer connection 140 is a separate component that is configured to be assembled onto a syringe 100, such as over the tip 126 of the syringe 100. The Luer connection 140 can comprise a ring 142 that is made of a material flexible enough to allow for radially expansion in the outward direction under pressure exerted on an inner wall 144 of the ring 142 when the central opening 148 of the Luer connection 140 is placed over the tip 126 of the syringe 100. The Luer connection 140 can include a plurality of ribs 143 that can extend radially outwards from the outer surface of the Luer connection 140. The ribs 143 can be arranged circumferentially around the Luer connection 140 so as to provide a texture that allows a label 110 and/or a film 250 to more easily engage the Luer connection 140, as will be described further below. Though one embodiment of the ribs 143 is shown, the present disclosure is not intended to be limited to such. In other embodiments, the outer surface of the Luer connection 140 is substantially smooth, i.e., lacking any ribs. In some embodiments, the inner surface of the Luer connection 140 comprises internal threads 149 configured to be engaged with outer threads 160 of a tip cap 150. In other embodiments, the inner surface of the Luer connection 140 is smooth.

In other embodiments, the Luer connection 140 is formed as an integral portion of the syringe 100, e.g., during a molding process. In such embodiments, the Luer connection 140 can extend from the distal end 100b of a syringe barrel body 103 along the axial direction A. At the center of the Luer connection 140 is included the tip 126 that that extends from the distal end 100b of the syringe barrel body 103 along the axial direction A. The tip 126 has an outer surface 126a and an inner surface 126b opposite the outer surface 126a, where the inner surface 126b defines a passage 132 that extends through the tip 126 to an outlet 135 of the tip 126. As the passage 132 and the outlet 135 are in fluid communication with the chamber 109 of the syringe 100, the passage 132 and the outlet 135 thus define the pathway for material being dispensed from the chamber 109 of the syringe 100.

Figure 3:
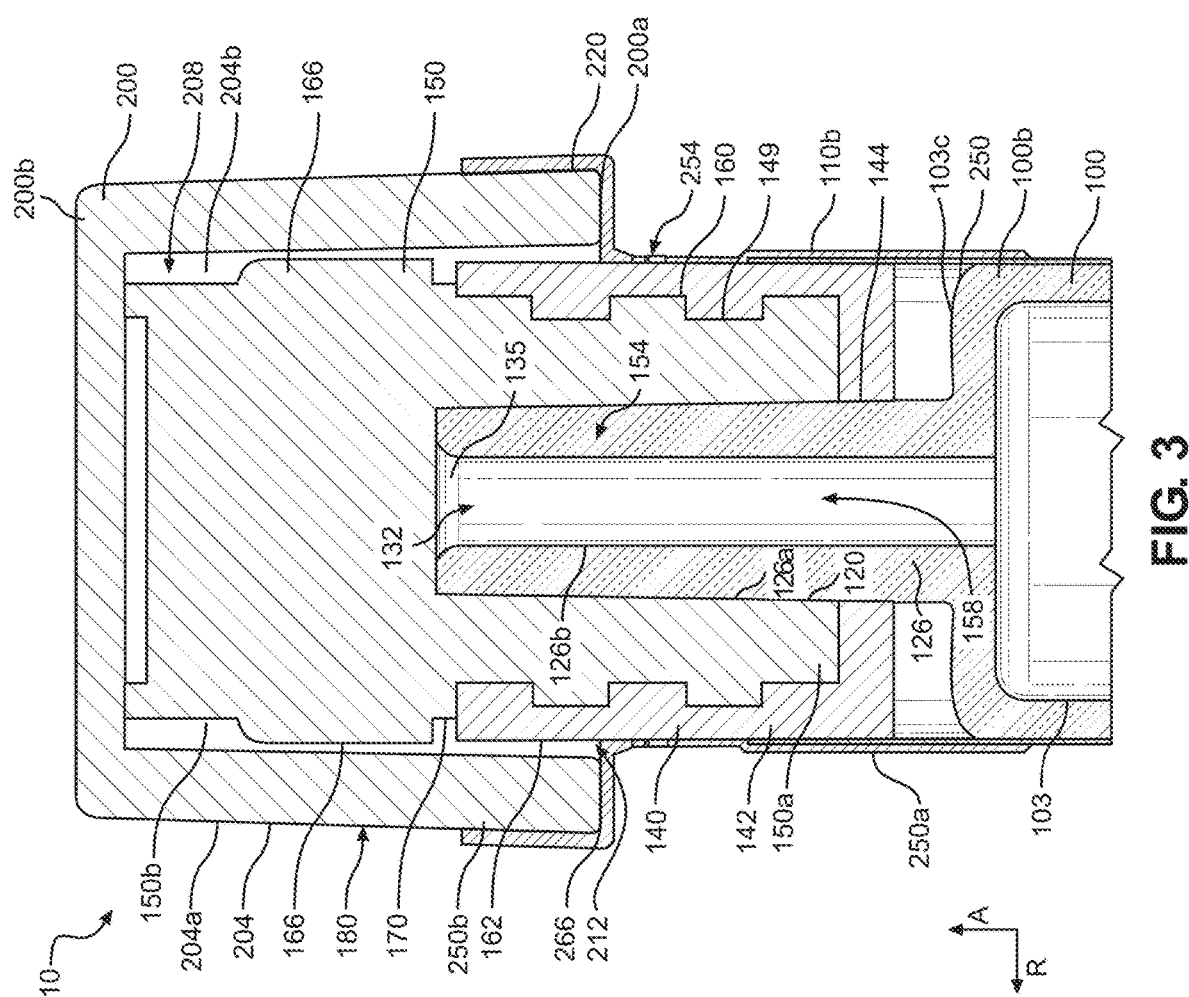
FIG. 3 illustrates a cross-sectional view of a distal portion of the syringe assembly shown in FIG. 1, taken along line 3-3 shown in FIG. 1.
Figure 4:
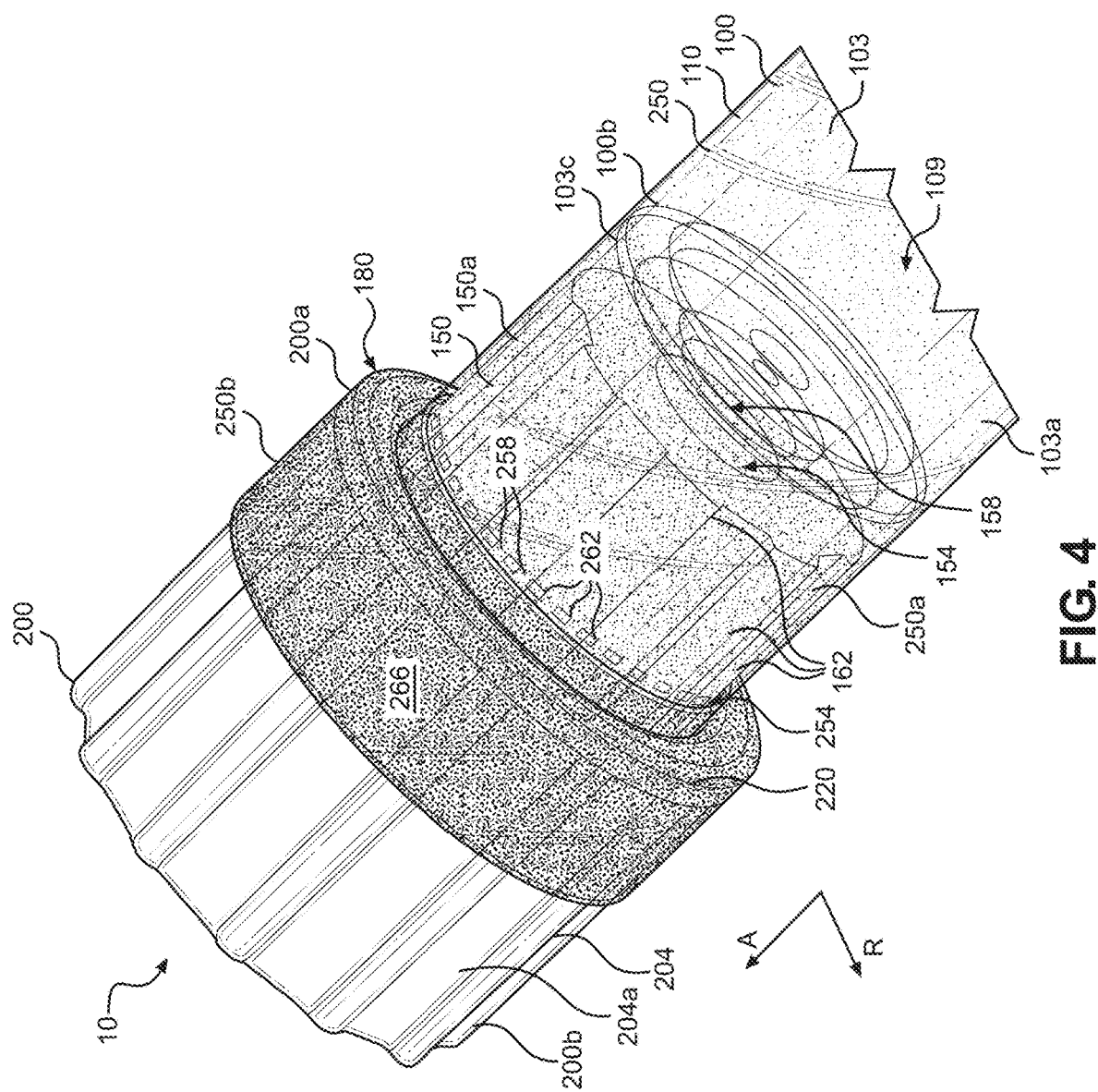
FIG. 4 illustrates a perspective view of the distal portion of the syringe assembly shown in FIG. 1.

In some embodiments, as depicted in FIG. 3, the assembly further comprises a label 110. In certain embodiments, the label 110 is continuous from a proximal end 110a to a distal end 110b opposite the proximal end 110a over at least a portion of the outer surface 103a of the syringe 100 and until at least a portion of the outer surface of the Luer connection 140. In other embodiments, the label 110 is continuous over at least a portion of the outer surface 103a of the syringe 100, the entire length of the outer surface of the Luer connection 140, and at least a portion of the outer surface of the tip cap 150. In such embodiments, the label 110 can be provided with an annular frangible connection, which must be broken in order to remove the tip cap 150 from the Luer connection 140. In some embodiments, as depicted in FIG. 3, a portion of the label 110 is imprisoned between a film 250 and the syringe 100 and/or between the film 250 and the Luer connection 140.

The label 110 can be attached to the syringe 100 and the Luer connection 140 (and, optionally, tip cap 150) by any suitable means. In some embodiments, the label 110 comprises a thermoplastic material and is attached to the syringe 100 and/or Luer connection 140 by heat-activated shrink wrapping. In certain embodiments, the label 110 comprises an adhesive and is attached to the syringe 100 and/or Luer connection 140 by applying pressure. In other embodiments, the label 110 is attached to the syringe 100 and/or Luer connection 140 by a combination of heat-activated shrink wrapping and an adhesive. In certain embodiments, the label 110 maintains the Luer connection 140 blocked in rotation and in translation with respect to the syringe 100 when the label 110 is attached. A preferred arrangement of a syringe 100, Luer connection 140, tip cap 150, and label 110 is described in U.S. Pat. No. 9,731,082, the contents of which are hereby incorporated by reference in its entirety.

The label 110 can be printed with information relating to the material contained within the chamber 109 of the syringe 100, e.g., active ingredient name, brand name, active ingredient concentration, volume, manufacturer, lot number, etc. The label 110 can also be bar coded with any combination of this information. The label 110 can be comprised of any suitable material, such as a thermoplastic material, paper, or a combination thereof. Thermoplastic materials that are suitable for a label 110 include, but are not limited to, polyvinyl chloride (PVC), polyethylene terephthalate (PET), oriented polystyrene (OPS), oriented polypropylene (OPP), polylactic acid (PLA) and mixtures thereof.

Continuing with FIGS. 1-4, the tip 126 extends from the distal end 100b of the barrel body 103 along the axial direction A. As depicted, the tip 126 can take the form of a substantially hollow tube, though other embodiments of the tip 126 are contemplated. The tip 126 can slightly taper inwards as it extends axially away from the distal surface 103c, or can alternatively define a substantially constant diameter. The tip 126 can have an outer surface 126a and an inner surface 126b that defines a passage 132 that extends through the tip 126. The passage 132 can extend from the chamber 109 of the syringe 100 to an outlet 135 of the tip 126. As the passage 132 and the outlet 135 are in fluid communication with the chamber 109, the passage 132 and the outlet 135 thus define a pathway for material being dispensed from the chamber 109 of the syringe 100. The passage 132 can take the form of a cylinder, a tapered tube, a stepped design, or any other suitable shape as desired.

After the syringe 100 has been filled, the outlet 135 needs to be sealed so as to prevent material from leaking out of the chamber 109. To do this, a tip cap 150 can be attached to the Luer connection 140 so as to seal the outlet 135. The tip cap 150 can extend from a proximal end 150a to a distal end 150b opposite the proximal end 150a along the axial direction A. As depicted, the proximal end 150a defines an opening 158, whereas the distal end 150b is closed. The tip cap 150 can define a central passage 154 extending along the axial direction A into the tip cap 150 from the opening 158. The tip cap 150 can further define a ridge 170 extending radially outwards from the outer surface of the tip cap 150, and substantially continuously around the entirety of the perimeter of the tip cap 150. In operation, the ridge 170 of the tip cap 150 abuts the distal end of the Luer connection 140 when the tip cap 150 has sealed the outlet 135. However, in other embodiments, the ridge 170 may only extend partially around the perimeter of the tip cap 150, or may not be present at all. Further, a plurality of ribs 166 can extend radially outwards from the outer surface of the tip cap 150 distal to the ridge 170. The ribs 166 can be arranged circumferentially around the tip cap 150 so as to provide a texture for grasping the tip cap 150 by a user of the syringe assembly 10. Though one embodiment of the ribs 166 is shown, the present disclosure is not intended to be limited to such.

In operation, the tip cap 150 is configured to be attached to the tip 126 of the syringe 100 so as to create a fluid seal over the outlet 135. To accomplish this, after the syringe 100 has been filled during assembly, the tip cap 150 can be screwed onto the Luer connection 140 such that the outer threads 160 of the tip cap 150 engage the internal threads 149 of the Luer connection 140. Alternatively, the tip cap 150 can be pushed into the Luer connection 140 with a force along the axial direction A, such that the tip cap 150 can be secured to the Luer connection 140 through an interference fit. When this is done, the tip 126 can be received within the central passage 154 of the tip cap 150 and continue to be disposed further through the central passage 154 until the tip 126 contacts the distal-most surface of the central passage 154, which indicates to the user that the tip cap 150 is completely secured to the syringe 100. At this point, the outlet 135 of the tip 126 can be disposed at the distal-most location in the central passage 154, thus creating a fluid seal over the tip 126. The ridge 170 can contact the upper surface of the outer wall of the Luer connection 140 so as to limit the extent to which the tip 126 can be disposed in the central passage 154. Once disposed into the Luer connection 140, the outlet 135 can be located at a distal-most part of the central passage 154 and the tip 126 can engage the inner surface of the tip cap 150, thus creating a fluid seal over the outlet 135.

Now referring to FIGS. 1-4, the tamper evident assembly 180 of the syringe assembly 10 will be discussed in detail. The tamper evident assembly 180 can include a tamper evident cap 200 and a film 250. The tamper evident cap 200 can include a main body 204 that extends from a proximal end 200a to a distal end 200b opposite the proximal end 200a along the axial direction A. The main body 204 can be configured as a substantially hollow cylinder, through other shapes are contemplated, as the shape of the tamper evident cap 200 can vary according to the shape of the syringe 100 and/or tip cap 150 of the particular syringe assembly 10 of which it is a part. The tamper evident cap 200 can be formed through injection molding, and can comprise a plastic such as medical grade polypropylene, polycarbonate, or polyethylene terephthalate. However, other methods of forming the tamper evident cap 200 and other materials for forming the tamper evident cap 200 are contemplated. The main body 204 defines an outer surface 204a and an inner surface 204b opposite the outer surface 204a, where the inner surface 204b defines a passage 208 configured to receive the Luer connection 140 and the tip cap 150. The distal end 200b of the main body 204 can be closed, whereas the proximal end 200a can define an opening 212, where the passage 208 extends from the opening 212 along the axial direction A and terminates within the main body 204 at a location proximal to the distal end 200b. However, it is contemplated that in other embodiments the distal end 200b of the main body 204 can be open.

The proximal end 200a of the main body 204 can define a ridge 220 that extends radially outwards from the outer surface 204a of the main body 204. The ridge 220 can extend circumferentially around an entirety of the main body 204, and can define the proximal-most portion of the tamper evident cap 200. However, in other embodiments the ridge 220 can be located elsewhere on the tamper evident cap 200 or extend to different extends about the tamper evident cap 200. The tamper evident cap 200 an also include a plurality of ribs 216 that extend radially outwards from the outer surface 204a of the main body 204 distal to the ridge 220, where the plurality of ribs 216 are positioned circumferentially about the outer surface 204a. The ribs 216 can define substantially hemispherical shapes, and can be spaced apart equidistantly about the circumference of the tamper evident cap 200. However, though one particular number and arrangement of ribs 216 is shown, other numbers and arrangements are contemplated. In operation, the ribs 216 can be configured to engage the film 250 so as to secure the film 250 to the tamper evident cap 200, as will be described further below. Although the tamper evident cap 200 is depicted to have a plurality of ribs 216 extending circumferentially around an entirety of the main body 204, other means for engaging with the film 250 are contemplated, such as alternative types of protrusions, patterns, and/or textures. In some embodiments, the type, pattern, and/or texture of the protrusions can be indicative of the type of material contained within the chamber 109 of the syringe 100. This allows the user of the syringe assembly 10 to easily determine what material is within the syringe 100 and helps avoid incorrect medicaments from being mistakenly applied to a patient.

In the depicted embodiment, the inner surface 204b is substantially smooth. However, in other embodiments, the inner surface 204b is textured or comprises one or more protrusions that extend radially inwards from the inner surface 240b. In one embodiment, the inner surface 204b comprises a plurality of ribs positioned circumferentially about the inner surface 204b that are configured to be positioned between complementary ribs 166 positioned circumferentially about the outer surface of the tip cap 150.

In operation, after the tip cap 150 is engaged with the Luer connection 140, the tamper evident cap 200 can be disposed over the tip cap 150. In some embodiments, when the tamper evident cap 200 is disposed over the tip cap 150, the tamper evident cap 200 is spaced in an entirety from the tip cap 150, the Luer connection 140, and the syringe 100. In other embodiments, when the tamper evident cap 200 is disposed over the tip cap 150, the tamper evident cap 200 is at least partially engaged with the tip cap 150, the Luer connection 140 and/or the syringe 100. For example, when disposed over the tip cap 150, the distal-most portion of the inner surface 204b of the tamper evident cap 200 can contact the distal-most surface of the distal end 150b of the tip cap 150. In other embodiments, the inner surface 204b of the tamper evident cap 200 can be engaged with the outer surface of the tip cap 150 and/or the outer surface of the Luer connection 140 along the axial direction A. Preferably, any contact between the tamper evident cap 200 and the tip cap 150 is such that the fluid seal over the outlet 135 is not compromised by the attachment of the tamper evident cap 200 and/or film 250 to the syringe 100 or by the disengagement of the tamper evident cap 200 from the syringe 100 upon breakage of the frangible connection 254 of the film 250.

In the depicted embodiment, the tamper evident cap 200 may not include any features so as to secure the tamper evident cap 200 to the tip cap 150, the Luer connection 140 and/or the syringe 100. As a result, the tamper evident assembly 180 can include a film 250 disposed over portions of the syringe assembly 10 to secure the tamper evident cap 200 to the Luer connection 140 and/or the syringe 100. The film 250 can define a body that extends from a proximal end 250a to a distal end 250b that is opposite the proximal end 250a along the axial direction A. In the depicted embodiment, the proximal end 250a of the film 250 can be disposed around a portion of the barrel body 103 of the syringe 100, while the distal end 250b of the film 250 can be disposed around a portion of the tamper evident cap 200. A portion of the film 250 between the proximal end 250a and the distal end 250b can also engage the tip cap 150 and/or the outer surface of the Luer connection 140.

In some embodiments, the film 250 is continuous through at least a distal portion of the syringe 100, the entire Luer connection 140, and at least a proximal portion of the tamper evident cap 200. In certain embodiments, the film 250 may extend on the syringe 100 for a length equal or more than 5 mm, e.g., 10 mm, 15 mm, 20 mm, 30 mm, or more, as measured from the distal end 100b of the syringe 100. Alternatively, or additionally, the film 250 may extend onto the syringe 100 for a length equal to or more than 10%, e.g., 20%, 40%, 60%, or more of the length of the syringe barrel body 103. In certain embodiments, the film 250 may extend on the tamper evident cap 200 for a length equal to or more than 2 mm, e.g., 3 mm, 4 mm, 5 mm, 6 mm, or more, as measured from the proximal end 200a. Alternatively, or additionally, the film 250 may extend onto the tamper evident cap 200 for a length equal to or more than 10%, e.g., 20%, 40%, 60%, or more of the length of the tamper evident cap 200. In other embodiments, the film 250 is continuous from at least a proximal portion of the Luer connection 140 to at least a proximal portion of the tamper evident cap 200, but does not cover any portion of the syringe 100. In yet other embodiments, the film 250 is continuous over the entire Luer connection 140 and at least a proximal portion of the tamper evident cap 200, but does not cover any portion of the syringe 100.

In operation, after the tip cap 150 engages the Luer connection 140 and the tamper evident cap 200 is disposed over the tip cap 150, the film 250 can be fitted over the tamper evident cap 200, the Luer connection 140 and/or the syringe 100 so as to secure the tamper evident cap 200 to the Luer connection 140 and/or the syringe 100. In particular, the ribs 216 that extend radially outwards from the outer surface of the tamper evident cap 200 can be configured to secure the distal end 250b of the film 250 to the tamper evident cap 200. Similarly, the ribs 143 that extend radially from the outer surface of the Luer connection 140 can be configured to secure a portion of the film 250 to the Luer connection 140. In one embodiment, the engagement between the film 250 and the tamper evident cap 200, the tip cap 150, the Luer connection 140, and/or the syringe 100 is formed by shrink-wrapping the film 250 over the tamper evident cap 200, the Luer connection 140, and/or the syringe 100. In some embodiments, the tamper evident cap 200 is disposed over the entirety of the Luer connection 140 such that the film 250 is secured to the tamper evident cap 200 and a distal end of the syringe 100, but the film does not directly contact the Luer connection 140. In such embodiments, the tamper evident cap 200 is secured to the Luer connection 140 indirectly, i.e., without any direct contact between the film 250 and the Luer connection 140. Further, the film 250 can be adhesive-bonded to the tamper evident cap 200. Additionally, the film 250 can be adhesive-bonded to the Luer connection 140 and/or the syringe 100. In addition to the above-described methods of attaching the film 250 to the other components of the syringe assembly 10, various other methods of attaching the film 250 may be utilized as desired.

To disengage the tamper evident cap 200 from the tip cap 150 and the syringe 100, the film 250 can include a frangible connection 254 positioned axially between the proximal and distal ends 250a, 250b of the film 250. The frangible connection 254 is configured to be the portion of the syringe assembly 10 that indicates to a user whether the syringe assembly 10 has been tampered with. When the film 250 secures the tamper evident cap 200 to the tip cap 150 and the syringe 100, the frangible connection 254 is configured to break under a force applied to the tamper evident cap 200. This force can be a clockwise or counter-clockwise rotational force, or any other force as desired. When the frangible connection 254 breaks, the tamper evident cap 200 is configured to disengage from the tip cap 150. As a result, the distal end 250b of the film 250 can remain attached to the tamper evident cap 200 and disengage from the remainder of the syringe assembly 10. If a user of the syringe assembly 10 sees that the frangible connection 254 of the film 250 is broken, the user knows that the material within the chamber 109 of the syringe 100 may have been tampered with. However, if the frangible connection 254 is intact, the user can be assured of a greatly reduced risk that the material has been tampered with. Further, breaking the frangible connection 254 can prevent the tamper evident cap 200 from being reattached to the tip cap 150.

As depicted, the frangible connection 254 can comprise a plurality of frangible bridges 258 positioned circumferentially around the body of the film 250. The frangible bridges 258 can be positioned around an entirety of the circumference of the film 250, such that when the frangible connection 254 breaks, the distal end 250b of the film 250 can be completely separated from the proximal end 250a. Each of the frangible bridges 258 can comprise a thin, elongate portion of the film 250 that defines a substantially constant width as they extend along the axial direction A. However, it is contemplated that each of the frangible bridges 258 can taper in width along the axial direction A. Further, the frangible bridges 258 can be equidistantly spaced about the circumference of the film 250, though various other spacing is contemplated. The frangible connection 254 can also define a plurality of gaps 262 that extend through the film 250 from its outer surface to its inner surface. Each of the gaps 262 can extend circumferentially between two adjacent frangible bridges 258. In the depicted embodiment, each of the gaps 262 defines a substantially rectangular shape. Though each of the gaps 262 is shown as having a particular design, each of the gaps 262 can vary in design and spacing along with the design and spacing of each frangible bridge 258. The inclusion of the frangible bridges 258 and gaps 262 allows the film 250 to be easily broken at the frangible connection 254. Though the frangible connection 254 is depicted to comprise a plurality of frangible bridges 258 positioned around an entirety of the circumference of the film, other methods of forming a frangible connection 254 are contemplated, such as tear strips or pull tabs.

The film 250 can be made of a thermoplastic material selected from the group consisting of polyvinyl chloride (PVC), ethylene vinyl acetate (EVA), polyethylene terephthalate (PET), oriented polystyrene (OPS), oriented polypropylene (OPP), polylactic acid (PLA) and mixtures thereof. In certain embodiments, the film 250 is made of PVC. In some embodiments, the interior surface of the film 250 or a portion thereof further comprises an adhesive material, such as a glue or a heat-activated adhesive. In certain embodiments, the interior surface of the distal end 250b of the film 250 to be disposed around a portion of the tamper evident cap 200 comprises an adhesive material.

The film 250 can be blank, or the film 250 can be printed with information relating to the material contained within the chamber 109 of the syringe 100, e.g., active ingredient name, brand name, active ingredient concentration, volume, manufacturer, lot number, etc. The film 250 can be fully transparent, partially transparent, or substantially opaque. The film 250 can also include a color-coded portion 266 that is indicative of the type of material contained within the chamber 109 of the syringe 100. This allows the user of the syringe assembly 10 to easily determine what material is within the syringe 100 and helps avoid incorrect medicaments from being mistakenly applied to a patient. In one embodiment, the color-coded portion 266 comprises a substantially solid band that defines at least a portion of the distal end 250b of the film 250 and extends circumferentially around the film 250. However, alternative placements, shapes, and sizes of the color-coded portion 266 are contemplated. The color of the color-coded portion 266 can be selected from a plurality of colors that each correspond to a different material. In one embodiment, the relationship between the color of the color-coded portion 266 and the material contained within the syringe 100 can conform to the labeling standards set by ASTM D4774, such that the color-coded portion 266 can be universally recognized and understood within any variety of medical environments. The standards set by ASTM D4774 are shown in the below table. The examples provided for each drug class are exemplary only and not meant to be exhaustive. Drugs that do not fit into the classes shown in Table 1 can be labeled with black printing on a white background according to ASTM D4774 standards. Exceptions are noted by the "A" superscript.

TABLE 1

ASTM D4774 Standards

| Drug Class | Examples | Pantone Color |
| --- | --- | --- |
| Induction Agents | Etomidate, Ketamine, Methohexital, Propofol, Thiamylal, Thiopental | Yellow |
| Benzodiazepines | Diazepam, Midazolam | Orange 151 |
| Benodiazepine Receptor Antagonist | Flumazenil | Orange 151 and White Diagonal Stripes |
| Muscle Relaxants (Depolarizer) | Succinylcholine[A] | Fluorescent Red 805 |
| Muscle Relaxants (Non Depolarizer) | Atracurium, Cisatracurium, Mivacurium, Pancuronium, Rocuronium, Vecuronium | Fluorescent Red 805 |
| Relaxant Antagonist (Non-Depolarizer) | Endophonium, Neostigmine, Pyridostigmine | Fluorescent Red 805 and White Diagonal Stripes |
| Narcotics | Alfentanil, Fentanyl, Hydromorphone, Meperidine, Morphine, Sufentanil, Remifentanil | Blue 297 |
| Narcotic Antagonists | Levallorphan, Naloxone | Blue 297 and White Diagonal Stripes |
| Vasopressors | Ephedrine, Norepinephrine, Phenylephrine, Epinephrine[A] | Violet 256 |
| Hypotensive Agents | Hydralazine, Nitroglycerine, Nitroprusside, Phentolamine, Trimethaphan | Violet 256 and White Diagonal Stripes |
| Local Anesthetics | Bupivacaine, Chloroprocaine, Lidocaine, Mepivacaine, Procaine, Ropivacaine, Tetracaine | Gray 401 |
| Anticholinergic Agents | Atropine, Glycopyrrolate, Scopolamine | Green 367 |
| Beta Blockers | Esmolol, Labetolol, Metroprolol | White Background with Copper 876U Bar Across Drug Name |
| Major Tranquilizers and Anti-Emetics | Droperidol, Inapsine, Haloperidol, Levomepromazine, Metoclopramide, Ondasetron | Salmon 156 |

[A]Printed against the background color as reversed plate letters with a black bar running from edge to edge of the film Though the film 250 is described as including a color-coded portion 266, it is also contemplated that in other embodiments all or a portion of the main body 204 of the tamper evident cap 200 defines a color-coded portion that is indicative of the type of material within the chamber 109 of the syringe 100 in combination with or in place of the color-coded portion 266. This can be done through molding the color-coded portion of the tamper evident cap 200 out of a material having the color that corresponds to the type of the material. Like the color-coded portion 266, the color-coded portion of the tamper evident cap 200 can comprise a color selected from a plurality of colors that each correspond to a different material. In one embodiment, the color-coded portion of the tamper evident cap 200 can conform to the labeling standards set by ASTM D4774.

Another embodiment of the present disclosure is a pharmaceutical product comprising a syringe assembly 10 and a secondary packaging system therefor. In some embodiments, the secondary packaging is a pouch, blister, flow wrapper, or bag. The secondary packaging can be comprised of an oxygen, light, and/or moisture barrier material, such as high-density polyethylene (HDPE), ethylene/vinyl alcohol copolymer (EVOH), polypropylene (PP), polyethylene terephthalate (PET), polyethylene naphthalate (PEN), and polyamide (PA), metalized film, aluminum foil, oxide coated films, and combinations thereof. In certain embodiments, the secondary packaging system also comprises an oxygen absorber. The oxygen absorber can be a sachet, pouch, canister, capsule, sticker, or strip that is placed inside of the secondary packaging. Alternatively, or additionally, the oxygen absorber can be incorporated into the material of the secondary packaging. In some embodiments, the oxygen absorber is selected from the group consisting of reduced iron compounds, catechol, ascorbic acid and analogs thereof, metal ligands, unsaturated hydrocarbons and polyamides.

Yet another embodiment of the present disclosure is a pharmaceutical product comprising a plurality of syringe assemblies 10 and a container therefor. In some embodiments, the container is a box, carton, case, package, tray, or tin. Optionally, one or more of the syringe assemblies 10 can be enclosed within a secondary packaging system before being placed into the container. In certain embodiments, each syringe assembly 10 enclosed within the container is filled with the same active ingredient. In other embodiments, each syringe assembly 10 enclosed within the container is filled with a different active ingredient from the same drug class, a different active ingredient from a different drug class, or any combination thereof. For example, the pharmaceutical product can comprise a plurality of syringe assemblies 10 enclosed with a container, wherein the two or more of the syringe assemblies 10 are filled with a different active ingredient from a first drug class, and one or more syringe assemblies 10 are filled with an active ingredient from a second drug class.

Figure 5:
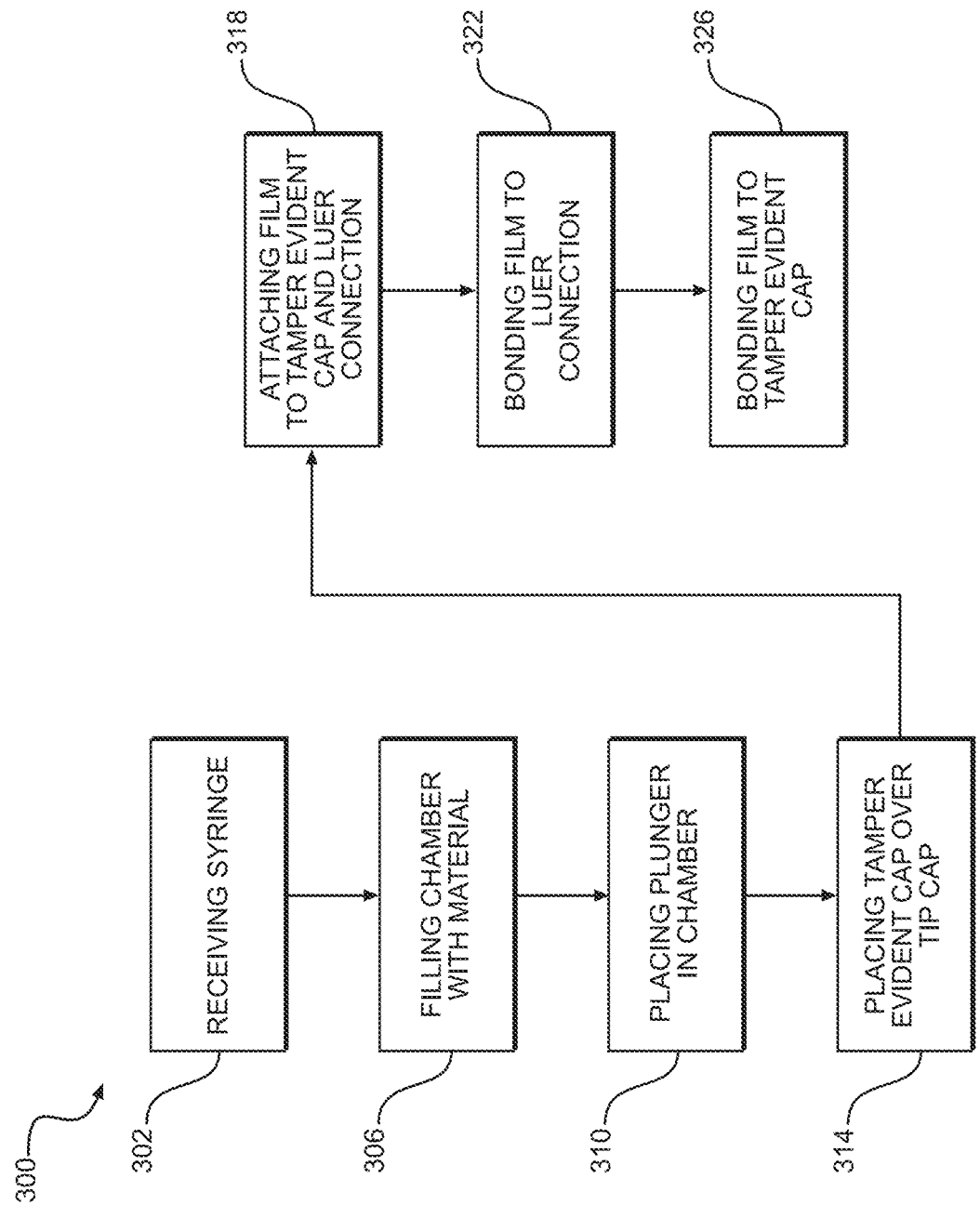
FIG. 5 illustrates a process flow diagram of a method of filling a syringe with a material according to an embodiment of the present disclosure.

Now referring to FIG. 5, a method 300 of filling the syringe 100 will be described. Method 300 begins with step 302, which comprises receiving the syringe 100, where the syringe 100 comprises the barrel body 103 extending from a distal end 100b having a Luer connection 140 and a tip 126 to an open proximal end 100a. As stated above, the barrel body 103 defines a chamber 109 that extends along the axial direction A therethrough. Further, the tip 126 is configured to be received within the central passage 154 of the tip cap 150, such that the inner surface of the tip cap 150 creates a fluid seal over the tip 126 and the outlet 135. Then, step 306 comprises filling the chamber 109 with the material through the proximal end 100a of the syringe 100. Next, in step 310, the plunger 50, which is connected to the plunger rod 25, is disposed within the chamber 109.

After step 310, step 314 involves placing the tamper evident cap 200 over the tip cap 150. In an alternative embodiment, step 314 can be performed after the syringe 100 and tip cap 150 are received and before the chamber 109 is filled with material. As stated above, though the distalmost portion of the inner surface of the tamper evident cap 200 may contact the distal-most portion of the outer surface of the tip cap 150 when the tamper evident cap 200 is placed over the tip cap 150, the contact between the tamper evident cap 200 and the tip cap 150 may not be sufficient to secure the tamper evident cap 200 to the tip cap 150. Accordingly, in step 318 the film 250 can be attached to the tamper evident cap 200 and the Luer connection 140 such that the film 250 secures the tamper evident cap 200 to the Luer connection 140. In step 318, the film 250 can also be attached to the syringe 100. As stated previously, the tamper evident cap 200 can include ribs 216 that promote a stronger engagement between the tamper evident cap 200 and the film 250, and the Luer connection 140 can include ribs 143 that promote a stronger engagement between the Luer connection 140 and the film 250. As a result, the film 250 can secure the tamper evident cap 200 to the Luer connection 140 and the syringe 100 until the frangible connection 254 of the film 250 is broken under a force applied to the tamper evident cap 200, at which time the tamper evident cap 200 can disengage from the tip cap 150.

In one embodiment, step 318 includes shrink-wrapping the film 250 over the tamper evident cap 200 and the Luer connection 140. However, other methods of attaching the film 250 to the tamper evident cap 200 and the Luer connection 140 are contemplated. To create a more secure engagement between the film 250 and the Luer connection 140, method 300 can include step 322, which involves bonding the film 250 to the Luer connection 140 and/or the syringe 100 via an adhesive. Additionally, to create a more secure engagement between the film 250 and the tamper evident cap 200, method 300 can include step 326, which involves bonding the film 250 to the tamper evident cap 200 via an adhesive. However, both of steps 322 and 326 are optional, as they can be each be performed in isolation, in conjunction with each other, or not at all. As stated above, the film 250 can also include a color-coded portion 266 that is indicative of the type of material contained within the chamber 109 of the syringe 100. The color of the color-coded portion 266 can be selected from a plurality of colors that each correspond to a different material. In one embodiment, the relationship between the color of the color-coded portion 266 and the material contained within the syringe 100 can conform to the labeling standards set by ASTM D4774, such that the color-coded portion 266 can be universally recognized and understood within any variety of medical environments.

In another embodiment, as shown in FIG. 6, a method 400 of filling the syringe 100 with a material begins with step 402, which comprises receiving the syringe 100. Then, step 406 comprises filling the chamber 109 of the syringe 100 with the material through the outlet 135 of the tip 126. After step 406, in step 410 the tip cap 150 is placed over outlet 135 of the tip 126 to create a fluid seal over the outlet 135. Next, in step 414, the tamper evident cap 200 is placed over the tip cap 150. To secure the tamper evident cap 200 to the tip cap 150, in step 418 the film 250 is attached to the tamper evident cap 200 and the syringe 100 as described above in the context of method 300.

In yet another embodiment of the invention, as shown in FIG. 7, a method 500 of applying the tamper evident cap 200 to the syringe 100, which is prefilled, is shown. Method 500 begins with step 502, in which the syringe 100 is received prefilled with a material and the tip cap 150 is already placed over the outlet 135 of the tip 126. Then, the tamper evident cap 200 is placed over the tip cap 150 in step 506. To secure the tamper evident cap 200 to the tip cap 150, in step 510 the film 250 is attached to the tamper evident cap 200 and the syringe 100 as described above in the context of method 300.

The material contained within the chamber 109 of the syringe 100 in the syringe assemblies 10 typically is a liquid, which can be aqueous, non-aqueous, or a combination of aqueous and non-aqueous liquids. In some embodiments, the liquid is a diluent intended for mixing with an active ingredient prior to administration to a subject. Exemplary diluents include, but are not limited to, water, 0.9% saline, 5% dextrose, Ringer's lactate solution, and other pharmaceutically acceptable diluents. In other embodiments, the liquid is a pharmaceutical formulation comprising an active ingredient and, optionally, one or more excipients. Thus, the invention provides a pharmaceutical product comprising a syringe assembly according to the present invention, wherein the liquid is a pharmaceutical formulation. Suitable excipients include, but are not limited to, a tonicity modifier, antioxidant, buffer, pH adjuster, preservative, solubilizer, stabilizer, or a combination of any of the forgoing. A diluent or pharmaceutical formulation can take on any suitable physical form including, but not limited to, solution, suspension, emulsion, or dispersion.

The active ingredient of the pharmaceutical formulation can be a therapeutic agent, a diagnostic agent, a nutrient, or a combination thereof. Examples of therapeutic agents include, but are not limited to antiinfectives, anesthetics, analgesics, anticoagulants, chemotherapeutics, hormones, antihypertensives, antiinflammatories, antiemetics, bronchodilators, adrenergics, immunoglobulins, antipsychotics, antidepressants, and combinations thereof. Examples of diagnostic agents include, but are not limited to x-ray, MRI and ultrasound contrast agents, cholecystokinetics, vasodilators, and combinations thereof. Examples of nutrients include, but are not limited to, salts, carbohydrates, minerals, vitamins, lipids, and combinations thereof.

In some embodiments, the active ingredient is a compound useful for pain management, muscle relaxation, sedation, and/or anesthesia. In certain embodiments, the active ingredient is an opioid, a benzodiazepine, a beta blocker, or an $\alpha_2$-adrenergic receptor agonist. In particular embodiments, the active ingredient is morphine, hydromorphone, hydrocodone, oxycodone, oxymorphone, codeine, buprenorphine, naloxone, naltrexone, fentanyl, remifentanil, sufentanil, alfentanil, meperidine, rocuronium, vecuronium, midazolam, lorazepam, diazepam, neostigmine, atropine, glycopyrrolate, dexmedetomidine, cisastracurium, ropivacaine, lidocaine, propofol, ketamine, succinylcholine, or a combination of the foregoing.

In other embodiments, the active ingredient is moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, decitabine, azacitidine, docetaxel, pemetrexed, palonosetron, aprepitant, fosaprepitant, famotidine, amiodarone, nitroglycerin, nicardipine, clevidipine, dobutamine, esmolol, labetalol, metroprolol, somatropin, liraglutide, abaloparatide, semaglutide, teriparatide, degarelix, sumatriptan, epinephrine, ephedrine, vasopressin, methotrexate, testosterone, hydroxyprogesterone, or a combination of the foregoing.

Figure 8:
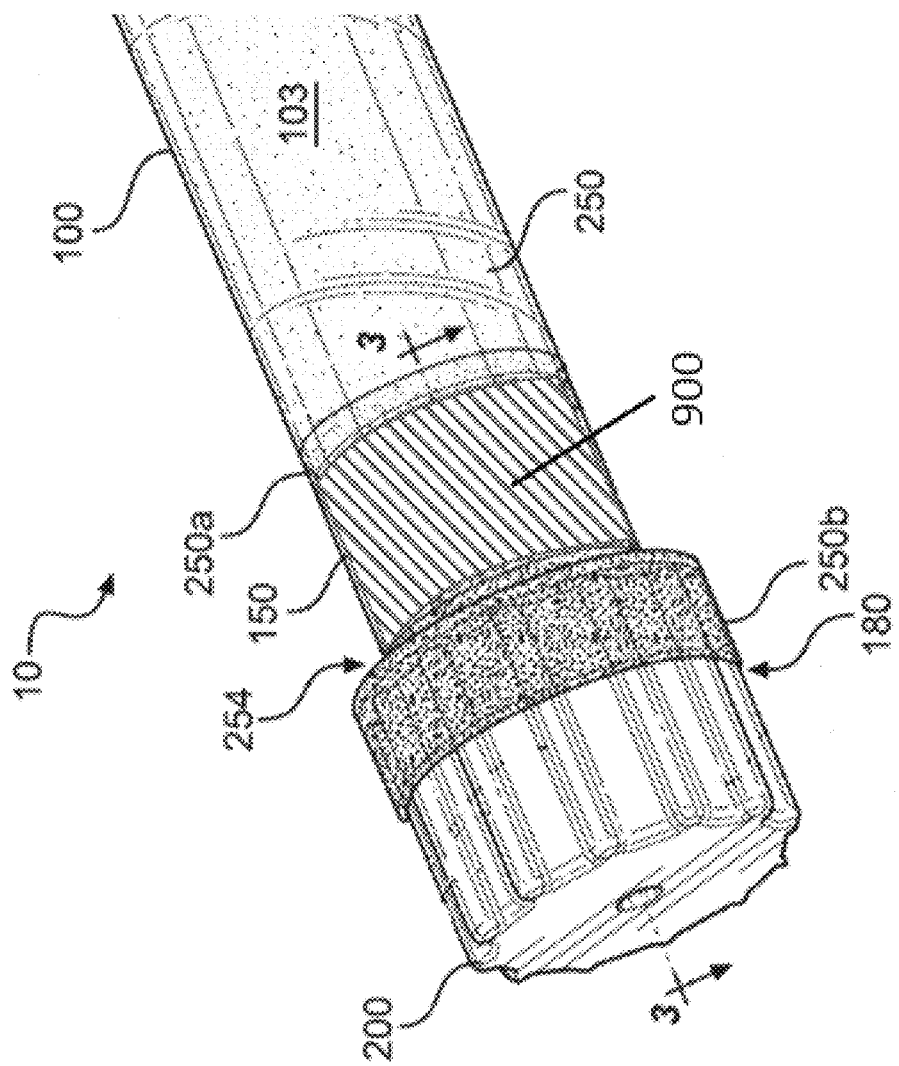
FIG. 8 illustrates a perspective view of a portion of a syringe assembly with an RFID tag in accordance with an embodiment of the present disclosure.

In yet another embodiment, as shown in FIG. 8, the syringe 100 can include one or more components for tracking, monitoring, and/or identifying the syringe assembly 10 and/or its contents. In some aspects, the film 250 disposed on the syringe 100 may include a radio frequency identification (RFID) label or tag 900. Signal communication to or from an RFID label is a form of wireless communication that uses radio waves to identify and track objects.

The RFID tag 900 may be configured to be affixed to the film 250 or, alternatively, may be part of a unitary component of the film 250. It will be appreciated that the RFID tag 900 can be utilized with any of the syringe assemblies disclosed throughout this application. The RFID tag 900 should be dimensioned and arranged relative to the syringe 100 such as to not interfere with the described structure or operation of the tamper evident cap 200 of any of the embodiments disclosed herein. In some aspects, the RFID tag 900 may be affixed to the syringe 100 separate from the film 250. In some aspects, an embodiment with the RFID tag 900 may be devoid of the film 250. In some aspects, the RFID tag 900 may be affixed to the tamper evident cap 200. In some aspects, the RFID tag 900 may be affixed to both, the syringe 100 and the tamper evident cap 200.

Figure 9A:
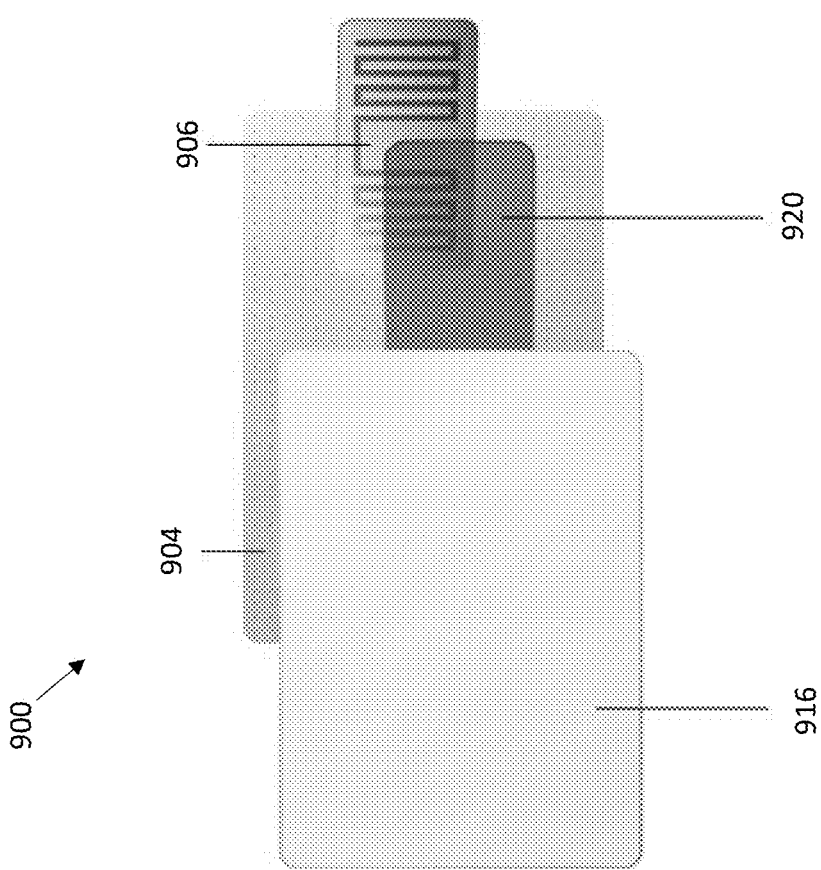
FIG. 9A illustrates an exploded perspective view of an RFID tag in accordance with an embodiment of the present disclosure.

Referring to FIG. 9A, the RFID tag 900 may include a backing 904 configured to be received on the syringe 100. The backing 904 may be secured to the syringe 100 via an adhesive or another suitable fixing mechanism. The backing 904 may include an adhesive thereon or, alternatively, may be configured to receive an adhesive between the syringe 100 and the backing 904. In some aspects, the film 250, as described throughout this application, may comprise the backing 904. The backing 904 may be a separate component of the film 250 or, alternatively, at least a portion of the film 250 may be used as the entire backing 904 of the RFID tag 900.

Figure 10A:
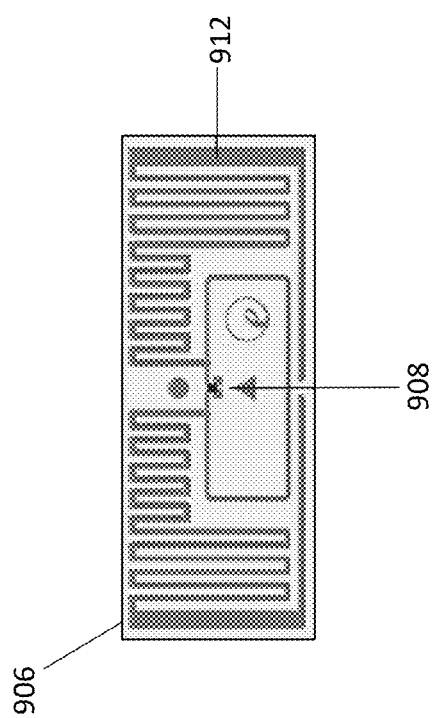
FIG. 10A illustrates a front perspective view of an RFID tag in accordance with an embodiment of the present disclosure.
Figure 10B:
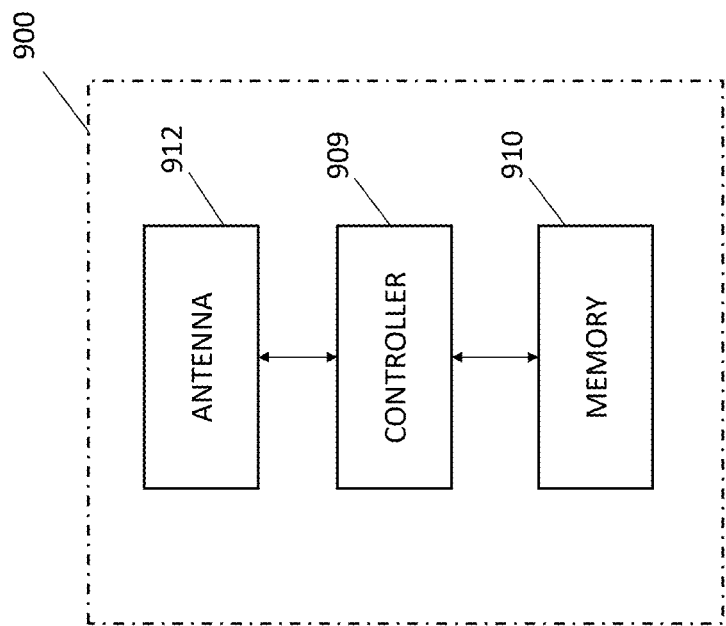
FIG. 10B illustrates a schematic of an RFID tag in accordance with an embodiment of the present disclosure.

The RFID tag 900 further includes an integrated circuit 908 that is connected to an antenna 912. The integrated circuit 908 is configured to store electronic data therein and to communicate with the antenna 912. Referring to FIG. 10B, the integrated circuit 908 may include a controller 909 and a memory 910. The memory 910 may include non-volatile memory and is configured for read/write access to receive, store, and allow access to electronic data transmitted to or from the RFID tag 900. The controller 909 is configured to read the electronic data from the memory 910 and to write electronic data to the memory 910. The controller 909 is configured to cause the antenna 912 to transmit the electronic data from the memory 910 to a reader 930 and to receive electronic data from the antenna 912 into the memory 910, as will be described in detail below. The antenna 912 is configured to communicate with the integrated circuit 908 and to transmit electronic data to and/or from the integrated circuit 908. The antenna 912 may be configured to supply power to the integrated circuit 908 sufficient to actuate the read/write process on the integrated circuit 908 to initiate transmission of the electronic data.

Figure 9B:
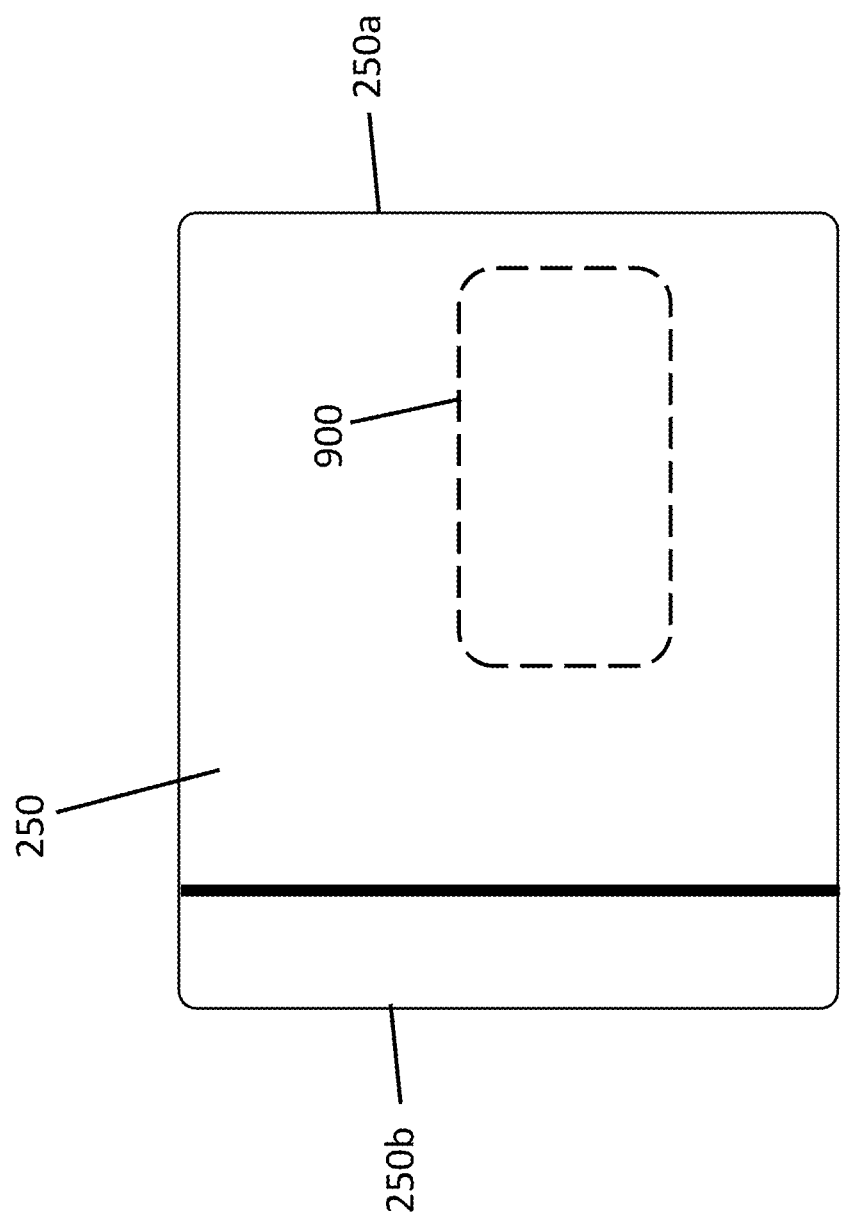
FIG. 9B illustrates a front perspective view of an RFID tag (shown in phantom) covered by a film in accordance with an embodiment of the present disclosure.

The integrated circuit 908 and/or the antenna 912 may be disposed on the backing 904, for example, opposite the syringe 100. In some aspects, the integrated circuit 908 and/or the antenna 912 may be adhered to the backing 904. In some aspects, the integrated circuit 908 and the antenna 912 may be secured relative to the syringe 100 by an external label 916. The external label 916 may be configured to adhere to the backing 904 (or the film 250) such that the integrated circuit 908 and the antenna 912 are held in friction fit between the external label 916 and the backing 904 (or the film 250). In some aspects, the external label 916 may be configured to contact the syringe 100 directly without contacting the backing 904 or the film 250. The external label 916 may include printed text, barcodes, graphics, or other visual identifiers thereon. Exemplary visual identifiers that have been described throughout this application with respect to the film 250 may also apply to the external label 916 and/or to the backing 904. In use, the RFID tag 900 may be hidden from view under the external label 916 or by the film 250 (see FIG. 9B). In some aspects, such as shown in FIGS. 9A and 10A, the integrated circuit 908 and the antenna 912 may be held together on an inlay layer 906. It will be understood that the inlay layer 906 serves to retain the integrated circuit 908 and the antenna 912 and may not be required for any other purpose in the RFID tag 900. With reference to embodiments disclosed throughout this application, in some embodiments, at least a portion of the RFID tag 900 (e.g., the integrated circuit 908 and the antenna 912) may be disposed between the film 250 and the syringe barrel body 103.

In some aspects, an intermediate layer 920 may be disposed between the external label 916 and the integrated circuit 908 and antenna 912. The intermediate layer 920 may provide structural and/or electromagnetic protection to the integrated circuit 908 and the antenna 912. The intermediate layer 920 may be disposed adjacent the inlay layer 906.

In some aspects, the backing 904 may be disposed such that the integrated circuit 908 and the antenna 912 are disposed between the backing 904 and the syringe 100. In such embodiments, the RFID tag 900 may include the additional external label 916 contacting the backing 904 opposite the integrated circuit 908 and the antenna 912, or, alternatively, such embodiments may be devoid of an external label 916 entirely.

Figure 11:
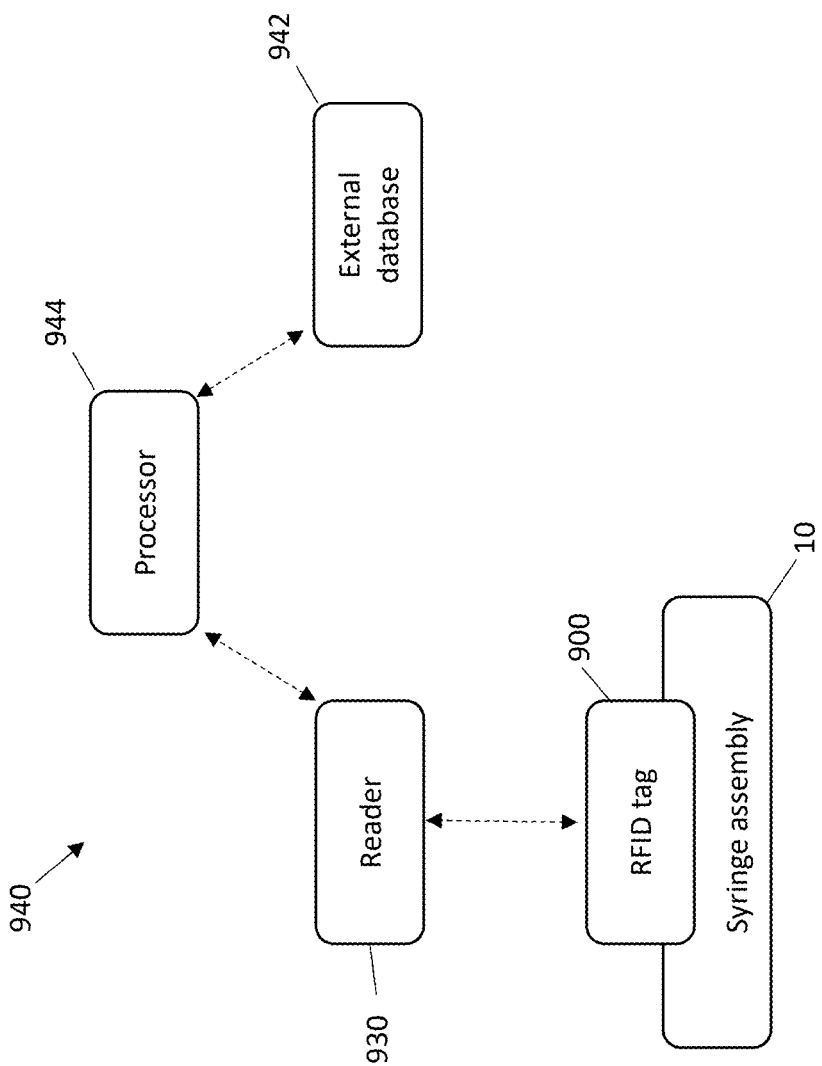
FIG. 11 illustrates a schematic of an RFID network in accordance with an embodiment of this disclosure.

The RFID tag 900 can be used to track and monitor the syringe assembly to which it is affixed, for example, the syringe assembly 10 as disclosed throughout this application. The RFID tag 900 can include active or passive RFID technology. In an active RFID system, the RFID tag includes a transmitter and a power source configured to activate the RFID tag and transmitter to broadcast an electronic signal with electronic data. The power source may include a battery or photovoltaic cell. In a passive RFID system, an RFID reader is configured to send a radio signal to the RFID tag. The antenna on the RFID tag can receive the signal and use that signal actuate transmittal of electronic data to/from the integrated circuit. The RFID tag 900 described herein can be designed and configured for either active or passive operation. It will be understood that if the RFID tag 900 is an active RFID tag, a transmitter and power source would need to be operationally connected thereto. In preferred embodiments, as shown in FIG. 11, the RFID tag 900 may be configured to interact with various components of a network 940. The RFID tag 900 can be a passive RFID tag that is configured to receive electronic power from an RFID reader 930. The reader 930 is configured to receive data from the RFID tag 900. Although referred to as a "reader," it will be understood that such a device may be configured to transmit data to the RFID tag 900. As such, the reader 930 may also be described as a writer 930. In some aspects, the reading and writing functionalities can be performed by a single device 930, which will be referred to as the reader 930. The RFID reader 930 is configured to provide the connection between the RFID tag 900 and an external system configured to send and/or receive information to and/or from the RFID tag 900. The external system may include a personal computing device, a network server, or a computing cloud. The RFID reader 930 is configured to communicate with the RFID tag 900 (or with a plurality of RFID tags 900) that are within the read/write range of operation. The RFID reader 930 is configured to perform various tasks, such as simple continuous inventorying, searching for RFID tags 900 that meet predetermined criteria, writing (or encoding) to selected RFID tags 900, or other electronic communications.

The RFID tag 900 can be designed to operate within known frequency ranges for RFID communication systems, including low frequency (LF), high frequency (HF), and ultra-high frequency (UHF). The LF band can cover frequencies from about 30 KHz to about 300 KHz. For RFID purposes, LF devices typically utilize either 125 KHz or 134.2 KHz frequencies. The LF band can be configured to operate within a range of up to approximately 10 cm for reading and/or writing from and/or to the RFID tag 900. The HF band can include frequencies in the range of from about 3 MHz to about 30 MHz and may be configured to operate within a range of up to approximately 100 cm. For RFID purposes, HF devices typically operate at 13.56 MHz. The UHF frequency band can cover frequencies from about 300 MHz to about 3000 MHz and may be configured to operate within a range of up to approximately 1200 cm. For RFID purposes, UHF devices typically operate at a range of between about 860 MHz to about 960 MHz (for passive RFID) and at about 433 MHZ (for active RFID). In some embodiments, the RFID tag 900 can be configured to operate at a frequency within the UHF spectrum although it will be appreciated that this disclosure is not limited to any particular frequency range.

The RFID tag 900 can receive, store, transmit, and/or otherwise make available information that is electronically stored therein, for example in the integrated circuit 908. With continued reference to FIG. 11, the reader 930 can further communicate with a processor 944 that is configured to communicate with data in a database 942 to provide instructions to the reader 930 to receive data from the RFID tag 900 or send data to the RFID tag 900, as well as to process the received data based on predetermined instructions. The RFID tag 900 can include various information, including at least a product identifier, product serial number, lot number, expiration date, or a combination of any of the above. The information can be sent to or received from the RFID tag 900 via the reader 930. In some embodiments, the RFID tag 900 can include at least all four of the product identifier, serial number, lot number, and expiration date. The serial number may be unique and may pertain to the individual syringe assembly or component thereof or, alternatively, to a particular type of assembly or medicament therein. The product identifier can refer to a graphical or alpha-numeric string of characters that represents the particular products to which the RFID tag 900 is attributed, for example, a syringe assembly 10 or a medicament within the syringe assembly 10. The product identifier may include a Global Trade Item Number (GTIN). The GTIN is an identifier for trade items that can be referenced within, or compared to, a database. In aspects where the RFID tag 900 is intended to correspond to a medicament, the GTIN may include a National Drug Code (NDC) that corresponds to a particular medicament or medicament component, such as a specific pharmaceutical compound. The particular NDC associated with a respective RFID tag 900 can be included in the NDC Directory maintained by the United States Food and Drug Administration (FDA). It will be appreciated that the GTIN may include a drug code that is different from the NDC, for example one that corresponds to a drug code directory outside of the United States. The RFID tag 900 may be designed to comply with one or more national or international standards for labeling, such as GSI and/or ISO. The RFID tag 900 may include the same information stored electronically within the integrated circuit 908 and appearing visually on the backing 904 or the external label 916.

In some aspects, the RFID tag 900 may receive some or all of the information detailed above at substantially the same time or, alternatively, may receive data over a plurality of write cycles, in which the data is electronically transmitted from the reader 930 to the RFID tag 900. In some aspects, the RFID tag 900 may be pre-encoded with the product identifier information and with the serial number prior to being applied to a syringe assembly, such as any of the assemblies described throughout this application. The RFID tag 900 may receive additional data, such as the lot number and expiration date, at a later time. In some aspects, some or all of the electronic data provided on the RFID tag 900 may be modified by the reader 930.

Figure 12:
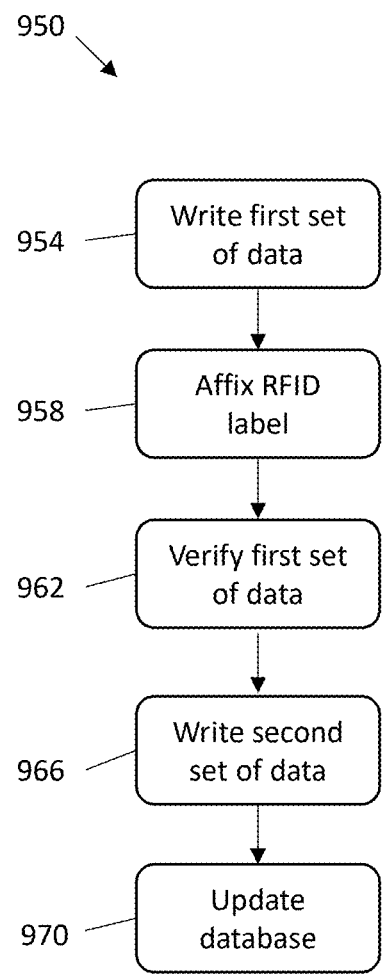
FIG. 12 illustrates a flow chart of a method of labeling a syringe assembly in accordance with an embodiment of this disclosure.

An exemplary encoding process 950 is depicted in FIG. 12. It will be appreciated that the RFID tag 900 may be encoded in a different process and that some of the steps described in the process 950 may be omitted, repeated, or changed in order relative to other steps. Referring to step 954, the RFID tag 900 is placed in electronic communication with the reader 930, and the reader 930 electronically transmits a first set of data to the RFID tag 900. The first set of data may include the product identifier and/or the serial number. The first set of data may be associated with a database 942 stored on the reader 930 or stored on an external computing device, server, network, or cloud and accessible by the reader 930. The database 942 is configured to communicate with the reader 930 via a processor 944. The processor 944 may be disposed on or in the reader 930 or on a separate computing device. The processor 944 and the database 942 may be disposed on the same device or on different devices. The processor 944 is configured to electronically communicate with the database 942 and with the reader 930. The electronic communication may be wired or wireless. The reader 930 is configured to transmit the signal to the antenna 912 of the RFID tag 900. The controller 909 in the integrated circuit 908 is configured to receive the signal from the antenna 912, encode or decode the signal according to preprogrammed instructions to generate storable data associated with the signal, and move the data associated with the signal to the memory 910 in the integrated circuit 908.

In step 958, the RFID tag 900 is then be applied to the syringe assembly 10 or another embodiment disclosed herein. The RFID tag 900 can be applied to the syringe 100 as described above. In some aspects, this step may be performed prior to step 954, such that the RFID tag 900 is affixed to the syringe 100 prior to the first set of data being transmitted to the RFID tag 900. Alternatively, this step may be performed later in the process 950, for example after the step 962 described below.

In step 962, the reader 930 is configured to be placed in electronic connection with the RFID tag 900 such that data can be transmitted between the RFID tag 900 and the reader 930. The reader 930 receives data that is stored on the RFID tag 900, for example the first set of data that may include the product identifier and/or the serial number that was transmitted to the RFID tag 900 in step 954. The controller 909 accesses the data stored on the memory 910, performed any necessary encoding or decoding step according to preprogrammed instructions, and sends the data to the reader 930 through the antenna 912. The reader 930 communicates the received information with a processor 944 configured to relate the received information with predetermined instructions, such as with a threshold, algorithm, or other computer programmed instruction. The processor 944 is configured to compare the received information per the predetermined instructions to determine if the information meets predetermined criteria. The comparison may be done with a predetermined set of data (for example a "control" set of data). In some aspects, the received set of data may include the first set of data that was transmitted to the RFID tag 900 in step 954, and the control set of data may include the same information as the first set of data. The comparison step may include determining if the received set of data matches the control set of data. If the information meets the criteria (e.g. if the received set of data matches the control set of data), the RFID tag 900 (and the assembly to which the RFID tag 900 is affixed) is considered to be "verified," and the process can continue to the next step. If the information received by the reader 930 in this step does not meet the predetermined criteria, the RFID tag 900 and the related assembly are not verified, and additional checking or verification steps may be performed. For example, if the RFID tag 900 is not verified, this could mean that the RFID tag 900 is damaged or improperly affixed to the syringe 100, in which case the RFID tag 900 may be replaced. In some aspects, lack of verification could mean that the first set of data transmitted to the RFID tag 900 in step 954 was not successful, in which case, step 954 may be repeated. In some aspects, the RFID tag 900 may have been tampered with, in which case the RFID tag 900 and/or any other component of the syringe assembly may be fixed or replaced.

In step 966, the reader 930 is configured to be placed in electronic connection with the RFID tag 900 (or remain in electronic connection with the RFID tag 900. The reader 930 is configured to transmit a second set of data to the RFID tag 900. The second set of data may include the lot number and/or the expiration date of the product or assembly. In some aspects, step 966 may be performed a plurality of times to transmit individual portions of data separately, for example, performed a first time to transmit the lot number to the RFID tag 900 and performed a second time to transmit the expiration date. It will be appreciated that additional information may be electronically transmitted to, and stored in, the integrated circuit 908 of the RFID tag 900.

In step 970, the reader 930 and/or the connected processor 944 may update a database with information pertaining to the RFID tag 900 processed in steps 954 to 966, for example to update inventory.

In some aspects, an additional step of printing visual indicators on the RFID tag 900 may be conducted. Although visual information does not affect the electronic reading or writing to the RFID tag 900, visual information may provide a level of redundancy to ensure that the necessary information appears on the label.

By using radio waves to encode the RFID tags 900 and then read information from those RFID tags 900, a user can track and monitor inventory without a visual line of sight. Because RFID readers 930 can receive electronic data from a plurality of RFID tags 900 simultaneously, less time can be spent on verifying individual tags (as would need to be done if utilizing a different tracking technique, such as visual inspection or barcode scanning). Information related to the RFID tags 900 can be stored in the database 942 and can be easily accessed. In some aspects, the database 942 may be configured to be updated automatically when information received by the reader 930 is different from the information stored in the database 942 with respect to the particular RFID tag 900 (i.e. with respect to the particular product identifier or serial number assigned to the RFID tag 900 or the syringe assembly). This allows for real-time updating of the database when a product with an RFID tag 900 is accessed, moved, or tampered with. In some aspects, a plurality of products may be disposed within a storage container, such as a cabinet. As the product is placed into the storage container, the reader 930 receives information related to the product, and the database 942 is updated to account for that product. If the product is removed from the storage container, the reader 930 no longer receives information related to that product and its affixed RFID tag 900. The database 942 may be updated to account for removal of that product.

By relying on RFID technology, inventory can be monitored and tracked more easily to ensure sufficient amount of desired products. Similarly, by monitoring expiration date, the inventory can be adjusted to remove expired products and ensure unexpired products are maintained at the desired quantities. Digitally monitoring and storing inventory information can also reduce information loss that often accompanies manual record keeping. Furthermore, as the process can be automated for all products, individual user approach differences are eliminated to increase precision in inventory management. Additionally, time spent on inventorying, locating expired products, and locating recalled lots is decreased. Using RFID technology further allows for immediate updating of the inventory when a product is removed and reduces chances of human error, such as when a user forgets to update inventory upon adding or removing a product. Additionally, monitoring how each tagged product or assembly is used, how often, how much, and in which circumstances can help users determine future inventory needs and/or efficacy of treatments. Information written to the RFID tag 900 can be validated through cGMP to ensure high quality and accuracy.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts, and features of the inventions—such as alternative materials, structures, configurations, methods, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features, and concepts may be expressly identified herein as being inventive or forming part of an invention, such identification is not intended to be exclusive, but rather there may be inventive aspects, concepts, and features that are fully described herein without being expressly identified as such or as part of a specific invention, the scope of the inventions instead being set forth in the appended claims or the claims of related or continuing applications. Descriptions of exemplary methods or processes are not limited to inclusion of all steps as being required in all cases, nor is the order that the steps are presented to be construed as required or necessary unless expressly so stated.

While the invention is described herein using a limited number of embodiments, these specific embodiments are not intended to limit the scope of the invention as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in a particular order as desired.

What is claimed is:

1. A syringe assembly, comprising:
   a syringe having a barrel body that extends from a proximal end to a distal end and defines a chamber extending along an axial direction therethrough, a Luer connection at the distal end, and a tip extending from the distal end along the axial direction and defining an outlet in fluid communication with the chamber, wherein the chamber contains a material;
   a plunger received within the chamber of the syringe to create a fluid seal within the barrel body;
   a tip cap defining a central passage configured to receive a portion of the tip such that the tip cap creates a fluid seal over the outlet;
   a tamper evident assembly, comprising:
      a tamper evident cap disposed over the tip cap, wherein the tamper evident cap has a main body that defines a proximal end defining an opening, a closed distal end opposite the proximal end along the axial direction, an outer surface, and an inner surface opposite the outer surface that defines a passage extending from the opening of the proximal end and configured to receive the tip cap; and
      a film including a frangible connection and configured to secure the tamper evident cap to the Luer connection; and
   a radio-frequency identification (RFID) tag configured to receive and store data related to the syringe assembly, wherein the RFID tag includes an integrated circuit, configured to store electronic information thereon, and an antenna operatively connected to the integrated circuit and configured to receive a signal from an RFID reader to cause transmission of at least part of the electronic information from the integrated circuit, and wherein the frangible connection is configured to break under a force applied to the tamper evident cap such that the tamper evident cap is configured to disengage from the Luer connection when the frangible connection breaks while maintaining the tip cap over the outlet of the tip following disengagement of the tamper evident cap.

2. The syringe assembly of claim 1, wherein the film is shrink-wrapped over a portion of the tamper evident cap and at least a portion of the Luer connection.

3. The syringe assembly of claim 1, wherein the film includes a color-coded portion that comprises a color selected from a plurality of colors that each correspond to a different material.

4. The syringe assembly of claim 3, wherein the color of the color-coded portion corresponds to the material in accordance with ASTM D4774.

5. The syringe assembly of claim 1, wherein the film is adhesive-bonded to the tamper evident cap.

6. The syringe assembly of claim 1, wherein the film is adhesive-bonded to the Luer connection.

7. The syringe assembly of claim 1, wherein the tamper evident cap includes a plurality of ribs extending radially outwards from the outer surface and configured to secure the film to the tamper evident cap.

8. The syringe assembly of claim 1, wherein the Luer connection includes a plurality of ribs extending outwards from an outer surface and configured to secure the film to the Luer connection.

9. The syringe assembly of claim 1, wherein a portion of the main body defines a color-coded portion that comprises a color selected from a plurality of colors that each correspond to a different material.

10. The syringe assembly of claim 1, wherein the tamper evident cap is spaced in an entirety from the syringe when the tamper evident cap engages the tip cap.

11. The syringe assembly of claim 1, wherein a portion of the tamper evident cap is in contact with the tip cap.

12. The syringe assembly of claim 11, wherein the fluid seal over the outlet is not compromised when the tamper evident cap is in contact with the tip cap.

13. The syringe assembly of claim 1, wherein the material includes an active ingredient that is (a) a therapeutic agent selected from a group consisting of anti-infectives, anesthetics, analgesics, anticoagulants, chemotherapeutics, hormones, antihypertensives, anti-inflammatories, antiemetics, bronchodilators, adrenergics, immunoglobulins, antipsychotics, and antidepressants or (b) a diagnostic agent selected from a group consisting of x-ray, MRI and ultrasound contrast agents, cholecystokinetics, and vasodilators.

14. The syringe assembly of claim 1, wherein the material includes an active ingredient selected from a group consisting of an opioid, benzodiazepine, α2-adrenergic receptor agonist, beta blocker, morphine, hydromorphone, hydrocodone, oxycodone, oxymorphone, codeine, buprenorphine, naloxone, naltrexone, fentanyl, remifentanil, sufentanil, alfentanil, meperidine, rocuronium, vecuronium, midazolam, lorazepam, diazepam, neostigmine, atropine, glycopyrrolate, dexmedetomidine, cisastracurium, ropivacaine, lidocaine, propofol, ketamine, succinylcholine, moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, decitabine, azacitidine, docetaxel, pemetrexed, palonosetron, aprepitant, fosaprepitant, famotidine, amiodarone, nitroglycerin, nicardipine, clevidipine, dobutamine, esmolol, labetalol, metroprolol, somatropin, liraglutide, abaloparatide, semaglutide, teriparatide, degarelix, sumatriptan, epinephrine, ephedrine, vasopressin, methotrexate, testosterone, and hydroxyprogesterone.

15. The syringe assembly of claim 1, wherein the film includes the RFID tag.

16. The syringe assembly of claim 1, wherein the RFID tag is a passive RFID tag and is configured to receive an electronic signal from the RFID reader to initiate transmission of the at least part of the electronic information.

17. The syringe assembly of claim 1, wherein the RFID tag is configured to operate at a frequency between 300 MHz and 3000 MHz.

18. The syringe assembly of claim 1, wherein the electronic information includes at least one of a product identifier, a serial number, a lot number, or an expiration date.

19. The syringe assembly of claim 1, wherein the RFID tag is disposed on the syringe.

20. The syringe assembly of claim 1, wherein the proximal end of the tamper evident cap is in contact with the barrel body.

21. The syringe assembly of claim 1, wherein the tamper evident cap is spaced in an entirety from the tip cap.

22. A tamper evident assembly, comprising:
a tamper evident cap having a main body that defines a proximal end defining an opening, a closed distal end opposite the proximal end along an axial direction, an outer surface, and an inner surface opposite the outer surface that defines a passage extending from the opening of the proximal end and configured to receive a tip cap and a Luer connection of a syringe;
a film including a frangible connection and configured to secure the tamper evident cap to the Luer connection; and
a radio-frequency identification (RFID) tag within the film and configured to receive and store data related to the syringe,
wherein the RFID tag includes an integrated circuit, configured to store electronic information thereon, and an antenna operatively connected to the integrated circuit and configured to receive a signal from an RFID reader to cause transmission of at least part of the electronic information from the integrated circuit, and
wherein the frangible connection is configured to break under a force applied to the tamper evident cap such that the tamper evident cap is configured to disengage from the Luer connection when the frangible connection breaks while maintaining the tip cap sealing the passage following disengagement of the tamper evident cap.

23. The tamper evident assembly of claim 22, wherein the frangible connection extends circumferentially around the tamper evident cap.

24. The tamper evident assembly of claim 22, wherein the film includes a color-coded portion that comprises a color selected from a plurality of colors that each correspond to a different material.

25. The tamper evident assembly of claim 22, wherein the electronic information includes at least one of a product identifier, a serial number, a lot number, or an expiration date.

* * * * *